(12) United States Patent
Sellergren et al.

(10) Patent No.: US 10,005,870 B2
(45) Date of Patent: Jun. 26, 2018

(54) CROSSLINKED POLYMERS PREPARED FROM FUNCTIONAL MONOMERS HAVING IMIDAZOLIUM, PYRIDINIUM, ARYL-SUBSTITUTED UREA OR ARYL-SUBSTITUTED THIOUREA GROUPS AND USES THEREOF

(71) Applicants: National University of Singapore, Singapore (SG); Börje Sellergren, Helsingborg (SE); Sudhirkumar Shinde, Malmö (SE)

(72) Inventors: Börje Sellergren, Helsingborg (SE); Sudhirkumar Shinde, Malmö (SE); Markus Rene Wenk, Singapore (SG); Federico Tesio Torta, Singapore (SG); Pradeep Narayanaswamy, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 19 days.

(21) Appl. No.: 15/118,225

(22) PCT Filed: Feb. 12, 2015

(86) PCT No.: PCT/SG2015/000043
§ 371 (c)(1),
(2) Date: Aug. 11, 2016

(87) PCT Pub. No.: WO2015/122845
PCT Pub. Date: Aug. 20, 2015

(65) Prior Publication Data
US 2017/0174812 A1    Jun. 22, 2017

(30) Foreign Application Priority Data

Feb. 12, 2014    (GB) .................................. 1402404.6

(51) Int. Cl.
*C08F 2/00* (2006.01)
*C08F 236/10* (2006.01)
(Continued)

(52) U.S. Cl.
CPC ............. *C08F 236/10* (2013.01); *B01J 20/26* (2013.01); *B01J 20/285* (2013.01);
(Continued)

(58) Field of Classification Search
CPC .... C08F 236/10; C08F 226/06; C08F 220/56; C08F 279/06; B01J 20/26; B01J 20/285; B01N 33/545
(Continued)

(56) References Cited

U.S. PATENT DOCUMENTS

| 4,600,578 A | 7/1986 | Pircio et al. |
| 4,649,048 A | 3/1987 | Johnson |

FOREIGN PATENT DOCUMENTS

| CN | 102050919 A | 5/2011 |
| DE | 4301801 A1 | 7/1994 |

(Continued)

OTHER PUBLICATIONS

Xiong, Y. et al., "One-step Synthesis of Thermosensitive Nanogels Based on Highly Cross-linked Poly(ionic liquid)s", Angew. Chem. Int. Ed., 2012, vol. 51, pp. 9114-9118.*
(Continued)

*Primary Examiner* — William K Cheung
(74) *Attorney, Agent, or Firm* — King & Schickli, PLLC

(57) ABSTRACT

The invention relates to a polymer obtainable by radical co-polymerization of a first monomer of general formula (I) or (II) or a mixture thereof: wherein A, A', B, B' X, Y, Y' and n are as defined herein; with a second, cross-linking monomer and optionally with one or more further co-monomers;
(Continued)

wherein the molar ratio of the first monomer to other monomers is less than or equal to 1:5. The polymers selectively bind to phosphate ester compounds and can be used as a solid phase in a method for isolating compounds comprising a phosphate ester group from a mixture comprising one or more phosphate monoesters and/or phosphate diesters and/or other compounds such as lipids.

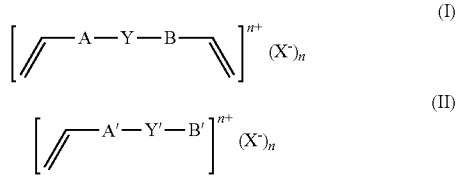

(I)

(II)

22 Claims, 11 Drawing Sheets

(51) Int. Cl.
    *C08F 226/06*     (2006.01)
    *C08F 220/56*     (2006.01)
    *C08F 279/06*     (2006.01)
    *B01J 20/26*     (2006.01)
    *B01J 20/285*     (2006.01)
    *G01N 33/545*     (2006.01)

(52) U.S. Cl.
    CPC .......... *C08F 220/56* (2013.01); *C08F 226/06* (2013.01); *C08F 279/06* (2013.01); *G01N 33/545* (2013.01)

(58) Field of Classification Search
    USPC ........................................................ 526/208
    See application file for complete search history.

(56) References Cited

FOREIGN PATENT DOCUMENTS

| EP | 016288 A1 | 5/1985 |
|---|---|---|
| WO | 2006/041370 A1 | 4/2006 |
| WO | 2009/064245 A1 | 5/2009 |

OTHER PUBLICATIONS

UKIPO Search Report—GB1402404.6, dated Aug. 10, 2014.
Sook Kyung Kim, et al., New Fluorescent Photoinduced Electron Transfer Chemosensor for the Recognition of H2P04, Organic Letters 2003, vol. 5, No. 12 pp. 2083-2086.
English Machine translation of DE 4301801 (BASF AG) Jul. 28, 1994.
PCT/SG2015/000043—International Search Report and Written Opinion of the International Searching Authority dated May 15, 2015.
Buscemi, R. et al., "Cross-Linked Imidazolium Salts as Scavengers for Palladium", ChemPlusChem, Published online Jan. 23, 2014, vol. 79, pp. 421-426.
Salamone, J. C. et al., "Synthesis and Homopolymerization Studies of Vinylimidazolium Salts", Polymer, 1973, vol. 14, pp. 639-644.
Agrigento, P. et al., "Highly Cross-linked Imidazolium Salt Entrapped Magnetic Particles—Preparation and Applications", J. Mater. Chem., 2012, vol. 22, pp. 20728-20735.
Sugii, A. et al., "High-performance Liquid Chromatography of Proteins on n-Methylpyridinium Polymer Columns", Journal of Chromatography, 1989, vol. 472, pp. 357-364.
English Machine translation of CN 102050919 A (Univ Northwest Normal) May 11, 2011.

* cited by examiner

| LCB-P | d14 | | | d15 | | | d16 | | | d17 | | | d18 | | | d19 | | | d20 | | | t18 | | | t20 | | |
|---|---|---|---|---|---|---|---|---|---|---|---|---|---|---|---|---|---|---|---|---|---|---|---|---|---|---|---|
| double bonds | 0 | 1 | 2 | 0 | 1 | 2 | 0 | 1 | 2 | 0 | 1 | 2 | 0 | 1 | 2 | 0 | 1 | 2 | 0 | 1 | 2 | 0 | 1 | 2 | 0 | 1 | 2 |
| S. cerevisiae | | | | | | | a | | | | | | | | | | | | | | | | a | | | a | |
| D. melanogaster | b | b | c | | | | b | b | | | | | | | | | | | a | | | a | | | | | |
| M. musculus lymph | | | | | | | | | | | | | d | d | | | | | | | | | | | | | |
| lymph node | | | | | | | | | | | | | d | d | | | | | | | | | | | | | |
| brain | | | | | | | | | | | | | e | e | | | | | f | | | | | | | | |
| plasma | | | | | | | | | | | | | e | e | | | | | | | | | | | | | |
| H. sapiens plasma | | | | | | | g | | | | | | g | g | | | | | | | | | | | | | |

Figure-12.

a   Ferguson-Yankey, S.R. et al. Yeast 19, 573-86 (2002)
b   Herr, D.R. et al. Development 130, 2443-2453 (2003)
c   Fyrst, I. et al. J Lipid Res 49, 597-606 (2008)
d   Nagahashi, M. et al. FASEB J 27, 1001-1011 (2013)
e   Saigusa, D. et al. Anal Bioanal Chem 7, 1897-905 (2012)
f   Morishige, J. et al. Rapid Comm Mass Spectrom 24, 1075-1084 (2010)
g   Quehenberger, O. et al. J Lipid Res 51, 3299-2205 (2010)

reported for the first time in this study
reported before in other biological material

CROSSLINKED POLYMERS PREPARED FROM FUNCTIONAL MONOMERS HAVING IMIDAZOLIUM, PYRIDINIUM, ARYL-SUBSTITUTED UREA OR ARYL-SUBSTITUTED THIOUREA GROUPS AND USES THEREOF

This application is the national stage of international patent application no. PCT/SG2015/000043 filed on Feb. 12, 2015 which in turn claims priority from British Patent Application No. 1402404.6 filed on Feb. 12, 2014, the disclosures of which are incorporated herein by reference in their entirety.

TECHNICAL FIELD

The present invention relates to polymers which selectively bind phosphate ester-containing compounds, and to a method for isolating phosphate ester-containing compounds from mixtures comprising one or more phosphate monoesters, phosphate diesters and/or other compounds such as lipids. In particular, the invention relates to a separation method in which long chain organic phosphate esters, for example phospholipids, are captured on a solid phase comprising a polymer of the invention and can be separately eluted. Other aspects of the invention relate to solid phases comprising the polymers and to separation devices comprising the solid phase.

BACKGROUND

Lipids are small molecules with large structural and chemical diversity. Over the past two decades, technologies such as chromatography and mass spectrometry have driven the biochemical analyses of complex lipid mixtures, tremendously advancing our knowledge of lipid diversity. Lipid extraction (preceding analysis), however, is still largely based on partitioning procedures developed in the 1950s. Although appropriate for many abundant components, these approaches result in variable recovery of the less-abundant and highly charged lipids, including phosphorylated signaling lipids.

Phosphate is common amongst biological lipids and present in either monoester and/or diester configurations, with most biologically active lipids containing at least one phospho-monoester. Sphingosine-1-phosphate (S1P) is an example of such a biologically active lipid. Long-chain amino alcohols, generally referred to as long-chain bases or LCBs (Pruett, S. T. et al. *J Lipid Res* 49, 1621-1639 (2008)), and their phosphorylated forms (LCB-P) display particularly diverse chemistries across biological species and tissues. In human plasma, the most abundant LCB-P is S1P, the phosphorylated derivative of [(2S, 3R, 4E)-2-aminooctadec-4-ene-1,3-diol], which has the structure:

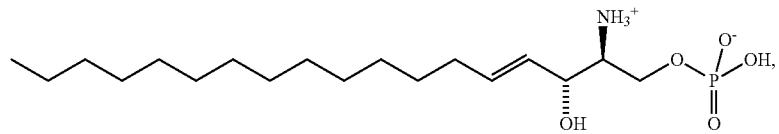 [SMILES: CCCCCCCCCCCCC/C=C/[C@@H](O)[C@@H]([NH3+])COP(=O)([O-])O]

S1P is currently emerging as a valid biomarker for life-threatening illnesses such as multiple sclerosis, cardiovascular disease and cancer. The commercially available method to detect S1P (antibody-based 'ELISA' kit) has the major disadvantages that only high S1P concentrations can be analysed and that there is a relatively high risk of false results because of the cross-reactivity of the antibodies with similar molecules. There is therefore a need for improved methods of detection of S1P. In addition to the more common LCB-Ps such as S1P, animal and plant cells and tissues comprise other LCB-Ps. Little is known about the existence of other LCB-Ps of different chemical and structural composition, despite the presence of various non-phosphorylated LCB precursors. In order to investigate the structures and functions of these compounds, it is necessary to isolate, quantify and characterize them.

Animal and plant cells and tissues also comprise other mono-phosphorylated compounds such as phosphoinositides (PIPs), phosphatidic acid, lysophosphatidic acid and ceramide-1-phosphate; phosphodiester compounds, for example phosphodiester lipids; and compounds such as lipids which contain neither phosphate mono-esters nor phosphate-diesters.

There is therefore a need to isolate, quantify and characterize phosphate ester-containing compounds such as phospholipids, particularly LCB-Ps, as well as phosphoinositides, phosphatitic acid, lysophosphatidic acid and ceramide-1-phosphate in the tissues and body fluids of humans and other animal species, for example mammals; and also in plants and microorganisms.

The present inventors have developed polymers which selectively bind phosphate esters.

SUMMARY

Therefore, in a first aspect of the invention there is provided a polymer obtainable by radical co-polymerisation of a first monomer comprising a compound of general formula (I) or (II) or a mixture thereof:

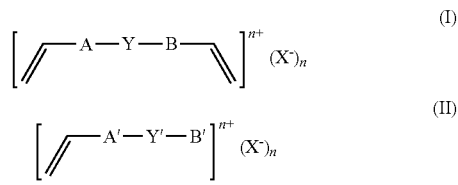

wherein each of A and A' is a 5- or 6-membered positively charged heteroaryl ring containing a quaternary nitrogen atom or when Y or Y' is —NR$^{20}$—(C=Z)—N—R$^{20}$—, A or A' is a 5- or 6-membered aryl or heteroaryl ring optionally substituted with halo, $C_{1-6}$ haloalkyl or nitro;

each of B and B' is a 5- or 6-membered positively charged heteroaryl ring containing a quaternary nitrogen atom; or a 5- or 6-membered aryl or heteroaryl ring optionally substituted with one or more substituents selected from halo, $C_{1-6}$ haloalkyl or nitro; each of Y and Y' is a linking group comprising 1-6 —CH$_2$— units wherein a —CH$_2$— unit is optionally replaced by a $C_{5-14}$ aryl or heteroaryl group optionally substituted with one or more substituents selected from H, halogen, $NH_2$, $C_{1-4}$ alkyl, $C_{1-4}$ alkoxy, $C_{1-4}$ haloalkyl or $C_{1-4}$ haloalkoxy or when each of A or A' and B or B' is a 5- or 6-membered aryl or heteroaryl ring optionally substituted with one or more substituents selected halo, $C_{1-6}$ haloalkyl or nitro, each of Y and Y' may be —$NR^{20}$—(C=Z)—N—$R^{20}$—, wherein each $R^{20}$ is independently H, methyl or ethyl; and Z is O or S;

n is 1 or 2 or when Y and Y' is —$NR^{20}$—(C=Z)—N—$R^{20}$—, n is 0; and $X^-$ is a halide ion or a hydrophobic anion such as $PF_6^-$;

with a second, cross-linking monomer and optionally with one or more further co-monomers;

wherein the molar ratio of the first monomer to the sum of the second monomer and the one or more further co-monomers (if present) is less than or equal to 1:5.

Polymers similar to the polymers of the present invention. For example Buscemi et al, ChemPlusChem, 79, 421-426 (2014) discloses palladium scavengers which are polymers prepared from monomers of the formula:

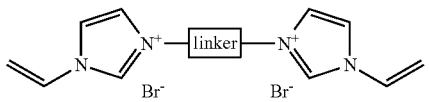

where the cross linker is one of the following:

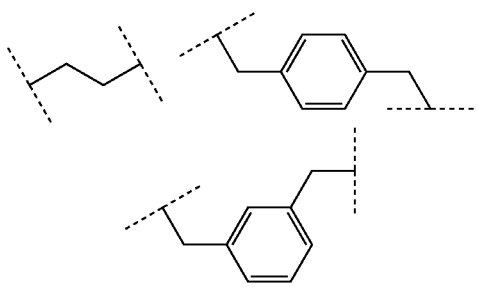

and wherein the monomer may be copolymerised in the presence of ethylene glycol dimethacrylate (EGDMA). However, this polymer differs from that of the present invention in that the ratio of the di-imidazolium monomer to EGDMA is 1:1. In contrast, the polymers of the present invention are prepared using a far higher proportion of the cross-linking monomer.

CN102050919 relates to polymer nanoparticles prepared from a monomer similar to those described by Buscemi et al except that the linker is —$(CH_2)_4$—, and EGDMA. These polymer nanoparticles are used for catalyzing the addition reaction of carbon dioxide to an epoxy ring compound. However, in these polymers the ratio of the imidazolium monomer to the cross-linking agent is from 2:1 to 10:1 whereas the polymers of the present invention are prepared using a far higher proportion of the cross-linking monomer.

Vinylimidazole-EGDMA copolymers are known from EP0162388, U.S. Pat. No. 4,600,578 and U.S. Pat. No. 4,649,048, which relate to the use of these polymers as bile acid sequestrating agents and for treating diarrhoea. However, the monomers from which these polymers are prepared differ in structure from the monomers used in the polymers of the present invention.

The polymer of the invention is capable of complexing phosphate ester groups, for example the phosphate groups of phosphorylated long-chain base phosphate molecules. Therefore, the polymer is suitable for use in detecting compounds comprising phosphate esters, for example LCB-Ps, and isolating them from biological samples.

Although low molecular weight bis-imidazolium hosts have been studied for the recognition of inorganic phosphate (Kim, S. K. et al. Org Lett 5, 2083-2086 (2003)), a polymer capable of binding long chain base phosphates has not previously been developed, nor have such hosts been used for the recognition and isolation of phospholipids.

The present invention has immediate relevance for our understanding of S1P biology as well as its therapeutic targeting. S1P biosynthesis, trafficking, receptor binding and degradation are highly controlled, and the targeting of S1P receptors and metabolizing enzymes remains an active field of research and drug development. It is conceivable that part of the LCB-P signaling machinery is influenced by the chemical nature of their aliphatic portion. This factor has so far been neglected, mainly because of the lack of information on S1P/LCB-P diversity. It is likely that LCB-P chain diversity affects receptor binding, and impacts S1P/LCB-P gradients, which are known to be important underlying components of immune cell trafficking via the reversible de-phosphorylation of S1P. Irreversible cleavage of S1P by S1P lyase, on the other hand, is a critical step that links sphingolipid metabolism with that of other lipids. The results from the sply−/− mutant demonstrate the unexpected accumulation of LCB-Ps when this single degradation step is impaired. Finally, it is possible that some of the chemically diverse LCBs (i.e., the non-phosphoryated precursor of the LCB-P described here) found in fungi, plants and insects could be substrates for kinases (in the respective organism, or in other organisms as a result of infection/diet) leading to even greater diversity among LCB-Ps. Our improved method for LCB-P analysis is therefore expected to have a profound impact in a variety of fields. Moreover, this technique can be also applied for the study of other low abundant signalling molecules (phosphate monoesters), broadening the number of its applications.

In the present invention the term "alkyl" refers to a straight or branched fully saturated hydrocarbon chain. $C_{1-6}$ alkyl groups have from one to six carbon atoms and examples include methyl, ethyl, n-propyl, isopropyl, n-butyl, isobutyl, tert-butyl, n-pentyl and n-hexyl. $C_{1-4}$ alkyl groups have from one to four carbon atoms.

The term "halo" refers to fluoro, chloro, bromo or iodo and a halide ion may be a fluoride, chloride, bromide or iodide ion.

The term "haloalkyl" refers to an alkyl group which is substituted by one or more halo atoms and includes any number of halo substituents up to perhalo substituted groups. Examples include trifluoromethyl; 1,1-dibromoethyl.

The terms "carbocyclyl" and "carbocyclic" refer to a non-aromatic cyclic group having three to ten ring atoms (unless otherwise specified), which may be fully or partially saturated and which may be fused or bridged. Examples include cycloalkyl groups such as cyclopropyl, cyclopentyl and cyclohexyl as well as cycloalkenyl groups such as cyclopentenyl and cyclohexenyl. Further examples include fused or bridged ring systems such as norbornane.

More suitable carbocyclic rings are 5- or 6-membered rings such as cyclopentyl, cyclohexyl or cyclohexenyl.

The terms "heterocyclyl" and "heterocyclic" refer to a cyclic group as defined above for carbocyclyl, except that one or more ring atoms is replaced by a hetero atom selected from N, O and S. Examples include aziridine, azetidine, pyrrolidine, pyrroline, imidazoline, piperidine, piperazine, morpholine, oxetane, tetrahydrofuran and oxazoline. Further examples include fused or bridged ring systems such as octahydroquinoline or nor-tropane.

More suitable heterocyclic rings are 5- or 6-membered rings such as piperidyl, piperazinyl, morpholinyl and tetrahydrofuryl.

The term "aryl" in the context of the present specification refers to a ring system with aromatic character having from 6 to 14 ring carbon atoms (unless otherwise specified) and containing one ring or two fused rings. Where an aryl group contains more than one ring, not all rings must be fully aromatic in character. Examples of aromatic moieties are benzene, naphthalene, anthracene, phenanthrene, tetrahydronaphthalene, indane and indene. More suitably, the aryl group is a phenyl group.

The term "heteroaryl" in the context of the specification refers to a ring system with aromatic character having from 5 to 10 ring atoms (unless otherwise specified), at least one of which is a heteroatom selected from N, O and S, and containing one ring or two fused rings. Where a heteroaryl group contains more than one ring, not all rings must be fully aromatic in character. Examples of monocyclic heteroaryl groups include pyridine, pyrimidine, furan, thiophene, pyrrole, pyrazole, imidazole, oxazole, isoxazole, thiazole and isothiazole. Examples of bicyclic fully aromatic heteroaryl groups include quinoline, isoquinoline, indole, benzofuran, benzimidazole and benzothiazole. Examples of bicyclic heteroaryl groups in which one ring is not fully aromatic in character include dihydroquinolines, tetrahydroquinoline, tetrahydroisoquinoline, chromene, chromane, benzimidazoline, benzomorpholine, isoindoline and indoline.

More suitable heteroaryl groups are monocyclic 5- or 6-membered rings such as pyridyl, furyl or thienyl.

In the present invention, the terms "phosphate monoester" and "phospho monoester" refer to compounds based on phosphoric acid ($H_3PO_4$) in which one of the hydrogen atoms is replaced by an organic group.

The terms "phosphate diester" and "phosphodiester" refer to compounds based on phosphoric acid ($H_3PO_4$) in which two of the hydrogen atoms are replaced by organic groups.

A long chain base phosphate molecule refers to a molecule having an alkyl, alkenyl or alkynyl chain of from 12 to 24 carbon atoms substituted with at least one phosphate group represented by the formula:

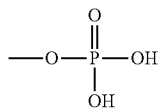

or a salt thereof.

Typically, a long chain organic phosphate molecule such as a phospholipid, for example a long chain base phosphate contains one to four phosphate groups, more usually one to three phosphate groups and in many cases one or two phosphate groups.

In addition to the phosphate group, a long chain organic phosphate molecule such as a long chain base phosphate molecule or other phospholipid may contain additional functional groups. For example, the chain may be substituted with one or more groups selected from $OR^{10}$, $NR^{11}R^{12}$ and $N^+R^{11}R^{12}R^{13}$, wherein each of $R^{10}$, $R^{11}$, $R^{12}$ and $R^{13}$ independently represents H or a $C_{1-4}$ alkyl group.

More suitably each of $R^{10}$, $R^{11}$, $R^{12}$ and $R^{13}$ independently represents H, methyl or ethyl, particularly H or methyl.

In the present application, long chain base phosphate molecules are referred to by the length of the carbon chain, the number of double bonds and the number of hydroxyl groups in the parent lipid, where "d" indicates dihydroxy and "t" indicates trihydroxy. Thus, sphingosine is denoted as d18:1 and phytosphingosine is t18:0.

The position of the double bond may be indicated by a superscript, i.e. 4-sphingenine is $d18:1^{\Delta 4t}$ or 4E-d18:1. The "d" or "t" relating to the parent lipid molecule is retained for the equivalent long chain base phosphate, where one of the OH groups has been replaced by the phosphate moiety. Thus, sphingosine-1-phosphate is also denoted as d18:1.

In some cases, polymers wherein A and B are both imidazolium groups, Y is —$(CH_2)_x$—, where x is 1-6 are excluded from the scope of the invention.

In some cases, polymers wherein A and B are both imidazolium groups, Y is —$(CH_2)_x$—, where x is 1-6 and wherein a —$CH_2$— unit is optionally replaced by a phenyl group are excluded from the scope of the invention.

In some cases, polymers wherein Y or Y' is —$NR^{20}$—(C=Z)—N—$R^{20}$— and A or A' is a 5- or 6-membered aryl or heteroaryl ring optionally substituted with halo, $C_{1-6}$ haloalkyl or nitro are excluded from the scope of the invention.

In the polymers of the invention, the molar ratio of the first monomer of general formula (I) or general formula (II) to the sum of the second cross linking monomer and one or more further co-monomers (if present) is less than or equal to 1:5. Typically the molar ratio is from about 1:100 to 1:5. More suitably, the molar ratio of monomer of general formula (I) or general formula (II) to cross linking monomer is from about 1:80 to 1:20; still more suitably from 1:65 to 1:25, or from 1:50 to 1:30. Typically the molar ratio is between 1:35 and 1:45, for example about 1:40.

Suitably, the polymer is obtainable by a polymerisation process in which the solvent is selected from a water, an alcoholic solvent such as methanol, ethanol or isopropanol, tetrahydrofuran (THF), acetone, dimethylformamide (DMF), acetonitrile (ACN), 1,1,1-trichloroethane, chloroform (CHCl3), dichloromethane (DCM), toluene, dimethylsulfoxide (DMSO), isopropanol or any mixture of these solvents or other solvents.

Typically, the solvent is a mixture of an alcoholic solvent and a non-polar organic co-solvent, for example toluene.

The most suitable polymers for use in the present invention are those in which the total concentration of the first monomer of formula (I) or (II) and the second cross-linking monomer and one or more further co-monomers (if present) is at least 100 mg/ml of solvent. More usually, the concentration of the monomers is from 100 to 500 mg/ml of solvent, for example 100-400 mg/ml, 100-300 mg/ml or 200-300 mg/ml. Typically, the total concentration of the monomers is about 250 mg/ml of solvent.

In monomers of general formula (I) or (II), $X^-$ is suitably a halide or a $PF_6^-$ ion. Typically $X^-$ is bromide.

In monomers of general formula (I) or (II) the linking group Y is suitably bonded to the quaternary nitrogen moiety of the group A or A'.

Suitably, the group A or A' is a pyridinium or imidazolium ion.

When A or A' is a pyridinium ion, the group —CH=$CH_2$ may be connected at the pyridinium 4-position.

When A or A' is an imidazolium ion, the group —CH=CH₂ may be linked to the non-quaternary ring nitrogen atom.

In one embodiment, the group B or B' is a 5- or 6-membered positively charged heteroaryl ring containing a quaternary nitrogen atom and in this embodiment: the linking group Y is suitably bonded to the quaternary nitrogen moiety;

the group B or B' may be a pyridinium or imidazolium ion.

When B is a pyridinium ion, the group —CH=CH₂ may be connected at the pyridinium 4-position;

when B is an imidazolium ion, the group —CH=CH₂ may be linked to the non-quaternary ring nitrogen atom.

In some suitable compounds A and B are the same and the monomer of general formula (I) is a compound of general formula (Ia) or (Ib):

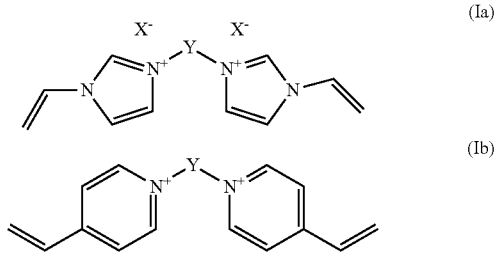

wherein X and Y are as defined above.

Monomers of formula (Ia) are particularly suitable for use in the present invention.

In an alternative embodiment, the group B or B' is a 5- or 6-membered aryl or heteroaryl ring, i.e. an uncharged moiety.

In this embodiment, B may be, for example, a phenyl or pyridyl group.

In suitable monomers of general formulae (I) and (II), Y is a linker group selected from:

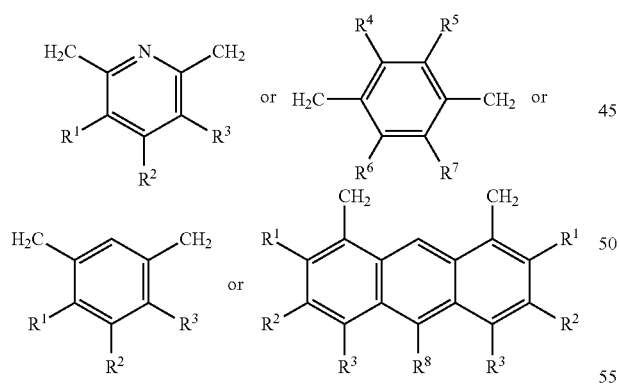

wherein each of $R^1$, $R^2$ and $R^3$ is independently selected from H, halogen, $NH_2$, $C_{1-4}$ alkyl, $C_{1-4}$ alkoxy, $C_{1-4}$ haloalkyl, $C_{1-4}$ haloalkoxy or $R^1$ and $R^2$ or $R^2$ and $R^3$ may together form a 5- or 6-membered carbocyclic, heterocyclic, aryl or heteroaryl ring;

each of $R^4$, $R^5$, $R^6$ and $R^7$ is independently selected from H, halogen, $NH_2$, $C_{1-4}$ alkyl, $C_{1-4}$ alkoxy, $C_{1-4}$ haloalkyl, $C_{1-4}$ haloalkoxy or $R^4$ and $R^5$ or $R^6$ and $R^7$ may together form a 5- or 6-membered carbocyclic, heterocyclic, aryl or heteroaryl ring;

$R^8$ is H, halogen, $NH_2$, $C_{1-4}$ alkyl, $C_{1-4}$ alkoxy, $C_{1-4}$ haloalkyl, $C_{1-4}$ haloalkoxy.

Monomers of general formula (I) or general formula (II) in which Y is

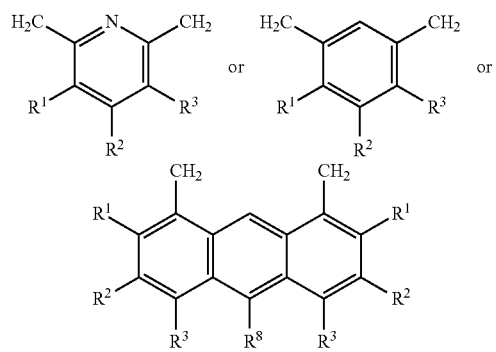

wherein each of $R^1$, $R^2$, $R^3$ and $R^8$ is as defined above; are more suitable.

Monomers of general formula (I) or (II), and especially monomers of general formula (Ia) above, in which Y is:

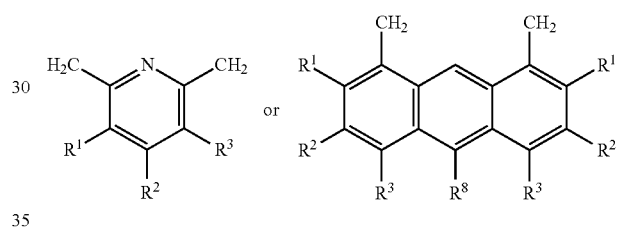

wherein each of $R^1$, $R^2$, $R^3$ and $R^8$ is as defined above are particularly suitable.

In one embodiment, in the first monomer of general formula (I) or (II), the linker Y is

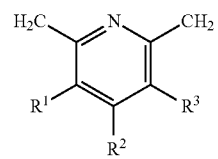

wherein $R^1$, $R^2$ and $R^3$ are as defined above.

Most suitably the monomer is a monomer of formula (Ia).

In this embodiment, suitably, $R^1$, $R^2$ and $R^3$ are hydrogen or $R^1$ and $R^2$ or $R^2$ and $R^3$ together form a 5- or 6-membered carbocyclic, heterocyclic, aryl or heteroaryl ring.

More suitably, $R^1$, $R^2$ and $R^3$ are all hydrogen.

A particularly suitable monomer of this embodiment is Monomer 1, which has the structure:

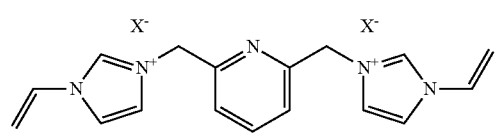

where $X^-$ is as defined above but is most suitably Br.

In an alternative embodiment, the linker Y is:

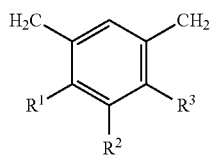

wherein $R^1$, $R^2$ and $R^3$ are as defined above.

In this embodiment, suitably, $R^1$, $R^2$ and $R^3$ are hydrogen or $R^1$ and $R^2$ or $R^2$ and $R^3$ together form a 5- or 6-membered carbocyclic, heterocyclic, aryl or heteroaryl ring.

More suitably, $R^1$, $R^2$ and $R^3$ are all hydrogen.

A particularly suitable monomer of this embodiment is Monomer 2, which has the structure:

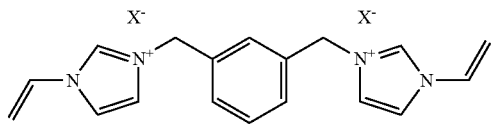

where $X^-$ is as defined above but is most suitably $Br^-$.

In an alternative embodiment, the linker Y is:

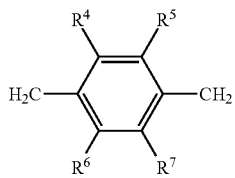

wherein $R^4$, $R^5$, $R^6$ and $R^7$ are as defined above.

In this embodiment, suitably, $R^4$, $R^5$, $R^6$ and $R^7$ are all hydrogen or $R^4$ and $R^5$ or $R^6$ and $R^7$ together form a 5- or 6-membered carbocyclic, heterocyclic, aryl or heteroaryl ring.

More suitably, $R^4$, $R^5$, $R^6$ and $R^7$ are all hydrogen.

A particularly suitable monomer of this embodiment is Monomer 3, which has the structure:

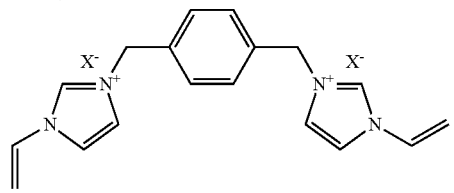

where $X^-$ is as defined above but is most suitably Br.

In another embodiment, Y is:

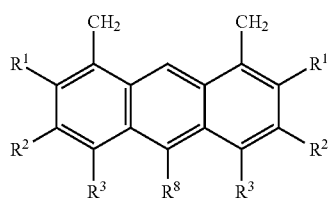

wherein $R^1$, $R^2$, $R^3$ and $R^8$ are as defined above.

In this embodiment, suitably, $R^1$, $R^2$, $R^3$ and $R^8$ are all hydrogen.

A particularly suitable monomer of this embodiment is Monomer 5, which has the structure:

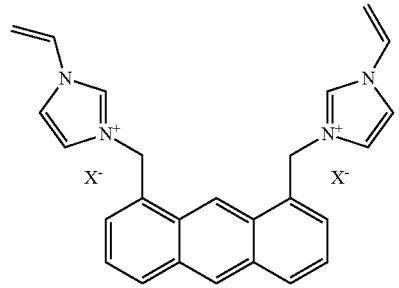

where $X^-$ is as defined above but is most suitably Br.

In a further alternative embodiment, the linker Y is 1-6 —$CH_2$— units. In particular, Y may be —$CH_2$—.

In the monomer of general formula (II), the linker Y may be 1-6 —$CH_2$— units and B may be a 5- or 6-membered heteroaryl ring, for example phenyl.

An example of a monomer of this embodiment is Monomer 4, which has the structure:

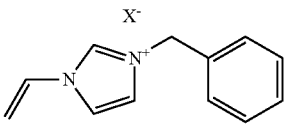

where $X^-$ is as defined above but is most suitably Br.

In another embodiment, the monomer of general formula (I) or general formula (II) may be a compound in which Y or Y' is —$NR^{20}$—(C=Z)—N—$R^{20}$—. In this embodiment, more suitably, independently or in combination:

$R^{20}$ is H or methyl but especially H; and/or

Z is O.

In such compounds each of A or A' and each of B or B' is 5- or 6-membered aryl or heteroaryl ring optionally substituted with one or more halo, $C_{1-6}$ haloalkyl or nitro substituents.

More suitably, each of A or A' and each of B or B' is a phenyl group optionally substituted with one or more halo, $C_{1-4}$ haloalkyl or nitro substituents, for example fluoro, trifluoromethyl or nitro substituents.

A particularly suitable example of a monomer of this type is Monomer 6:

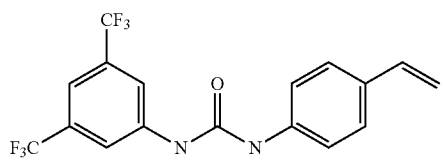 [SMILES: C=Cc1ccc(NC(=O)Nc2cc(C(F)(F)F)cc(C(F)(F)F)c2)cc1]

The polymer of the invention may be prepared from a single monomer of general formula (I) or general formula (II) or from two or more such monomers.

In one embodiment, a monomer of general formula (I) or (II) in which Y or Y' is —$NR^{20}$—(C=Z)—N—$R^{20}$—, may be combined with another monomer of general formula (I) or (II) in which Y or Y' is other than is —$NR^{20}$—(C=Z)—N—$R^{20}$—.

Suitable monomers for use in such combinations are those described above. In particularly suitable combinations, a monomer selected from Monomer 1, Monomer 2, Monomer 3, Monomer 4 or Monomer 5 may be combined with Monomer 6.

In some cases, one of the monomers for the preparation of the polymer may exhibit a change in fluorescence on binding of a phosphate ester and this property may be carried through into the polymer so that binding of a phosphate ester to the polymer can be detected as a quenching or an enhancement of the fluorescence emission of the polymer.

In some cases, the monomer which exhibits this property may be the monomer of general formula (I) or (II), for example, a monomer in which the linker Y or Y' is an anthracene group or a monomer in which the linker Y or Y' is —$NR^{20}$—(C=Z)—N—$R^{20}$—. Examples of monomers are Monomer 5 and Monomer 6.

Monomers of general formulae (I) and (II) are known and are readily available or may be prepared by methods familiar to those of skill in the art, for example the methods set out in Examples 1, 6, 8, 10 and 11 below, or adaptations thereof which would be clear to a person of skill in the art.

Cross linking monomers which are suitable for use in the present invention include di- and tri-methacrylate monomers, dialkenyl benzene monomers and bis acrylamide monomers.

Specific examples of cross linking monomers include ethyleneglycol dimethacrylate (EGDMA), divinylbenzene (DVB), diisopropenylbenzene, (DIB), trimethylolpropanetrimethacrylate (TRIM), pentaerythritoltriacrylate (PETA), ethylenebisacrylamide (EBA), piperazinebisacrylamide (PBA), and methylenebisacrylamide (MBA).

EGDMA is particularly suitable.

In some cases, the polymer will be the product of the monomer of general formula (I) or (II) without further co-monomers.

In other cases, however, one or more further co-monomers are added to the mixture of first monomer and second, crosslinking monomer. The particular co-monomer which is chosen will depend upon the nature of the cross linking monomer. Thus, when the cross linking monomer is a di- or tri-methacrylate such as EGDMA, TRIM, or MBA, the co-monomer may be also be a methacrylate monomer, for example methyl methacrylate, 2-hydroxyethylmethacrylate, methacrylamide or an alternative $C_{1-6}$ alkyl methacrylate so that a methacrylate matrix is produced.

When the cross linking monomer is a dialkyl benzene-based monomer such as DIB, it is more appropriate to select an alkenyl benzene monomer such as styrene as the co-monomer in order to produce a suitable matrix. Similarly, an acrylamide co-monomer for use in combination with an acrylamide cross linking monomer.

Polymers formed from Monomer 1 or combinations of Monomer 1 with other monomers of general formula (I) or general formula (II) have been shown to be particularly suitable, especially polymers formed from Monomer 1 co-polymerised with EGDMA. The inventors have demonstrated that imprinted resins formed from Monomer 1 copolymerised with EGDMA bind a greater proportion of a phosphate ester anion in a neutral buffer such as HEPES (4-(2-hydroxyethyl)-1-piperazineethanesulfonic acid) buffer, pH 7, compared with similar imprinted resins formed from Monomers 2, 3 or 4. Thus the copolymer formed from Monomer 1 bound 89% of the available phosphate compared with 58% and 34% respectively for polymers formed from Monomers 2 and 3.

The polymerisation reaction may be conducted at a temperature of from 40° C. to 90° C., more usually about 40° C. to 80° C. In one embodiment, the temperature is maintained at about 40° C. to 60° C., for example about 50° C. for a period of 12 to 48 hours, for example about 24 hours, following which it is raised to about 65° C. to 75° C., for example about 70° C. for a further period of 2 to 6 hours, for example about 4 hours.

The binding polymer of the invention is suitably a macroporous polymer such that the structure contains large pores or channels. Macroporous polymers are highly cross-linked polymers which contains large interconnected pores or channels within their structure. Unlike hydrogels and similar polymers, which require hydration in order for pores to form, the pores and channels in a macroporous polymer are formed during the polymerisation process and are present at all times. Macroporous polymers are known in the art and are described, for example, by Arrua et al, (Materials 2009, 2, 2429-2466).

The polymer, after crushing and sieving, can be used as a binding polymer to extract phosphate esters, including phospholipids, from a biological sample.

As discussed above, the polymer is obtainable by radical co-polymerisation and therefore in a further aspect of the invention there is provided a process for the preparation of a novel polymer as described above, the process comprising the radical co-polymerisation of a first monomer of general formula (I) or general formula (II) as defined above with a second, cross-linking monomer; characterised in that the ratio of the first monomer to the second monomer is less than or equal to 1:5.

Suitably, the molar ratio of the first monomer of general formula (I) to the second cross linking monomer is as described above and the reaction temperature and conditions are also as described above for the first aspect of the invention.

Usually, the polymerisation reaction will be initiated using a polymerisation initiator. Examples of suitable polymerisation initiators include azo-N,N'-bisdimethylvaleronitrile (ABDV), azo-N,N'-bisisobutyronitrile (AIBN), 2,2'-azobis-(2,4-dimethyl-4-methoxyvaleronitrile) (V70) or any other azo-based initiator (available from Wako Pure Chemical Ind. Ltd., (Japan); or redoxinitiators e.g. ammoniumpersulfate with or without added accelerator (e.g. TEMED=tetramethylethylenediamine). The choice of initiator is not critical and any known polymerisation initiator could be used.

As described above, the process may further include the addition of a co-monomer.

The reaction may be conducted in any suitable solvent such as water, methanol, ethanol, tetrahydrofuran (THF), acetone, dimethylformamide (DMF), acetonitrile (ACN), 1,1,1-trichloroethane, chloroform ($CHCl_3$), dichloromethane (DCM), toluene, dimethylsulfoxide (DMSO), isopropanol or any mixture of these or other solvents.

More suitably, the reaction is conducted in a solvent comprising a mixture of an alcoholic solvent and a non-polar organic co-solvent. Suitable alcoholic solvents include methanol, while toluene is an example of a suitable co-solvent.

Suitably in this case, the alcoholic solvent and the non-polar organic solvent are present in a ratio of 1:5 to 5:1 v/v, more suitably 1:1 v/v.

Suitably, the polymerisation reaction is conducted under an inert atmosphere, for example nitrogen or argon.

The temperature conditions for the reaction are also as described above.

In addition to macroporous polymers, however, the polymer can also be prepared in other formats such as nanofibers, nanotubes, monoliths, nanoparticles and their nanostructured counterparts such as core shell nanoparticles with optionally different functional properties such as magnetic or luminescent cores or labeled with probes allowing facile detection (e.g. electrochemiluminescent probes ECL). They can be tuned to exhibit maximum compatibility with the surrounding medium e.g. coatings to minimize protein adsorption. The polymer can be produced by any technique available for producing polymer particles including techniques relying on polymerisations in liquid-liquid two phase systems by suspension polymerisation or emulsion polymerisation or any variant of these (e.g. miniemulsion polymerisation), or in one liquid phase by dispersion polymerisation or precipitation polymerisation.

In one embodiment, the polymerisation reaction is performed using controlled radical polymerisation (CRP), which differs from conventional radical polymerisation in respect of the life time of the propagating radicals. In CRP this can be extended to hours which allows the preparation of polymers with predefined molecular weights, low polydispersity, controlled composition and functionality. This leads to polymers displaying higher binding capacity, affinity and faster association and dissociation of peptide. Common CRP techniques are RAFT (reversible addition fragmentation chain transfer polymerisation), ATRP (atom transfer radical polymerisation) and iniferter (initiator, transfer, termination) polymerisation.

In some cases, it is possible to produce polymer particles by grafting a polymer film onto the surface of a preformed support. The grafting can be performed according to either the "grafting to" or the "grafting from" approach, both of which are well known to those of skill in the art. The latter approach improves the production process as well as the molecular recognition and kinetic properties of the materials (and is described in U.S. Pat. No. 6,759,488).

In other cases, polymer particles according to the invention may be produced using a molecular imprinting approach in which a template resembling a phosphate ester target molecule in shape and functionality is added to a mixture of the first monomer and the second, cross-linking monomer prior to polymerization. In the present case, the template will usually be a monomer resembling a target phosphate monoester compound such as a LCB-P. Suitable LCB-P templates include PL-CL14 or a salt thereof, for example a mono- or di-alkali metal salt, such as a mono- or di-lithium, sodium or potassium salt. A mono- or di-sodium salt is particularly useful. After polymerization, the template may be removed from the polymer to leave a structure which exhibits affinity for the target phosphate monoester compound or compounds.

In another embodiment the polymer can be produced in the form of nanoparticles in a typical size range of 10 nm-500 nm. The engineering of nano-micrometer-sized polymer particles can be done by precipitation polymerisation (F. Wang, P. A. G. Cormack, D. C. Sherrington and E. Khoshdel, *Angew. Chem. Int. Ed.* (2003) 42(43), 5336-5338) or miniemulsion polymerisation procedures where uniform imprinted beads can be produced prepared by high dilution polymerisation in one step. Both aqueous and non-aqueous protocols can be used.

Alternatively, nanoparticle synthesis can be performed by grafting (N. Perez-Moral, A. G. Mayes, Macromol, Rapid Commun. 2007, 28, 2170). This starts from a nonporous nanosized core containing radical initiator or chain transfer groups. Onto the core a thin polymer films can be grafted with minimal influence of the bead size, dispersity and morphology on the polymerisation conditions. Nanoparticles can thus be engineered which can capture their target in biological fluids. Paramagnetic, monosized polymer particles, are commonly used for this purpose. The technique is fast, mild and involves no centrifugation or chromatography. Paramagnetic particles may be prepared in the form of core/shell microgels by a two-stage "seed-and-feed" precipitation polymerisation or by grafting a polymer shell on a magnetic core bead.

The polymers of the present invention are capable of selectively binding phosphate esters and therefore in a further aspect of the invention there is provided a method for isolating compounds comprising a phosphate ester group from a sample, the method comprising:

i. contacting the sample with a first solvent so as to extract soluble compounds into a sample solution, wherein the first solvent is capable of dissolving phosphate ester compounds;

ii. contacting the sample solution with a solid phase comprising a polymer according to the first aspect of the invention;

iii. washing the solid phase with one or more washing solvents to remove compounds not comprising a phosphate ester group; and iv. eluting compounds comprising a phosphate ester group with either or both of a basic elution solvent and an acidic elution solvent.

In the method of the invention, the biological sample may be derived from any species of animal, plant or microorganism. The sample may be a tissue sample from a mammal, including a human. Suitable samples blood, plasma and lymph or other tissues, including brain tissue. Blood and tissue samples from other animal species may also be used or, in some cases, for example with small animals such as insects, the sample may comprise the entire organism. The sample may also be derived from a plant and may include material taken from any part of the plant, including leaves and seeds. In some cases, the sample will be a microorganism, for example bacteria or yeast such as *Saccharomyces cerevisiae*.

The solid phase may be incorporated into a separation device which itself forms a further aspect of the invention as will be discussed below.

Suitably, the first solvent comprises an alcoholic solvent such as methanol, ethanol, n-propanol or isopropanol, particularly methanol, although in some circumstances a chlorinated solvent such as dichloromethane or chloroform may also be used. The soluble compounds extracted by the first solvent include not only compounds comprising phosphate monoesters, for example long chain base phosphates, and phosphate diesters but also other many other types of compound, including the lipids from which many long chain base phosphate compounds are derived. Therefore it is necessary to separate phosphate monoester- and phosphate diester-containing compounds from one another and from these other compounds.

Once the sample has been loaded onto the solid phase or device containing the polymer of the invention, molecules which are non-specifically bound to the solid phase can be eluted using the one or more washing solvents. The washing solvent or solvents may also comprise alcoholic solvents and, for example, may be selected from methanol, ethanol, n-propanol and isopropanol or mixtures thereof.

In one embodiment, the solid phase is washed firstly with isopropanol followed by a mixture of isopropanol and methanol in a ratio of 1:1 v/v.

In step (iv), the phosphate esters are eluted with either or both of a basic elution solvent and an acidic elution solvent.

The acid elution solvent is useful for removing phosphate monoesters from the solid phase and in some cases, for example when the method is intended for the isolation of phosphate monoesters, for example phospholipids such as S1P, the acidic elution solvent may be used alone without the basic elution solvent.

Although the basic elution solvent may also be used alone, the process more suitably, includes its use in combination with the acidic elution solvent.

When a basic elution solvent and an acidic elution solvent are employed, the basic elution solvent may be used prior to the acidic elution solvent.

In step (iv) the acidic elution solvent suitably comprises a mixture of a chlorinated solvent and an alcoholic solvent. The chlorinated solvent may be, for example, chloromethane, dichloromethane or chloroform, with chloroform being particularly suitable. Examples of suitable alcoholic solvents include methanol, ethanol, n-propanol and isopropanol, but especially methanol.

Suitably, the ratio of chlorinated solvent to alcoholic solvent in the elution solvents is 1:1 v/v and thus one suitable example of an elution solvent is an acidified 1:1 v/v mixture of chloroform and methanol.

Acidification of the acidic elution solvent may be achieved using an organic acid, for example formic acid or trifluoroacetic acid. One example of a particularly suitable acidic elution solvent is a mixture of chloroform/methanol/1% trifluoroacetic acid. Suitably these are in a volume ratio of 49.5/49.5/1.

The acidic elution solvent removes the phosphate monoester compounds from the binding polymer and the elution rate differs for different phosphate monoesters.

The basic elution solvent may comprise an alcoholic solvent or mixture of alcoholic solvents together with a basic compound such as an amine, especially a tertiary amine, for example a trialkyl amine such as triethylamine or trimethylamine. Suitable basic elution solvents include mixtures of isopropanol and methanol, for example a 1:1 mixture, and a tertiary amine. Where the basic compound is a tertiary amine the solvent may be isopropanol/methanol/amine, suitably in a volume ratio of 49.5/49.5/1. Triethylamine is a particularly suitable basic compound for use in such mixtures.

Using the method of the present invention it is possible to separate the phosphate monoesters from phosphate diesters and other compounds and also to separate them from one another. The separated phosphate ester compounds may be further characterized, for example using mass spectrometry. Thus, even if full identification of the compounds is not possible, a mass can be obtained.

Mass spectrometry either may be carried out simultaneously with the chromatography step, for example using an LC-MS apparatus, or after the chromatography step.

In some cases a standard solution may be added to the sample solution before step (ii). The standard solution may comprise one or more known phosphate ester compounds, for example phosphate monoesters such as long chain base phosphate compounds, and may therefore assist with the identification of similar compounds, e.g. long chain base phosphate compounds, in the sample. Usually, the amount as well as the identity of phosphate oester compounds in the standard is known and this will enable the quantitative detection of the long chain base phosphates and other phosphate ester compounds in the sample.

In one embodiment, the method comprises the additional step of derivatising the phosphate ester compounds of the sample, for example by reacting with an alkylating agent in order to replace one or more of the hydrogen atoms on a phosphate or an amine group with an alkyl group. This method is particularly useful for the separation of phosphate monoester compounds.

Derivatisation is suitably carried out after contacting the sample with the solid phase. However, if the phosphate ester compounds are derviatised after the elution step (iv) it is preferable to repeat steps (ii) to (iv) using a mixture of the derivatised phosphate ester compounds as the sample.

Suitably the alkylating agent is a methylating agent, for example trimethylsilyl diazomethane (TMS-diazomethane).

The derivatisation step is particularly suitable when the sample comprises two or more similar phosphate ester compounds, especially phosphate monoester compounds, and more especially LCB-Ps. In this case, the inventors have found that derivatisation led to a gain in sensitivity, possibly explained by a more effective ionization of the alkylated derivatives. This is particularly true for long chain base phosphate compounds containing an amine group, which, when alkylated, carries a permanent positive charge while the negative charge on the phosphate is neutralised.

By introducing and optimizing the above two steps (phospho-monoester capture via the binding polymer and derivatization with TMS), the inventors have:

(i) improved the signal intensity of LCB-Ps derived from plasma by ~60-fold compared with LC-MS alone;

(ii) reduced matrix interference; and (iii) eliminated the carry-over effects commonly encountered with LC-MS of native LCB-Ps (see Berdyshev, E. V., Gorshkova, I. A., Garcia, J. G., Natarajan, V. & Hubbard, W. C. *Anal Biochem* 339, 129-136 (2005)).

This enhanced workflow led to the discovery of previously undescribed LCB-P species unable to be detected/quantified by LC-MS alone.

This new detection method was further validated in various biological matrices for its accuracy and precision, reproducibility and linearity. Moreover, the number of species detected and their relative abundance was conserved after the derivatization reaction. The aforementioned characterizations involved nano-electrospray ionization and high-resolution MS after chromatographic separation of the mixtures by Hydrophilic Interaction Chromatography (HILIC) built into a microfluidic chip. This was important to improve the co-elution of S1P standards and endogenous LCB-Ps for qualitative and quantitative characterizations[6] of new LCB-P species. Indeed, few high-resolution mass spectra of LCB-Ps have been published, possibly because of the low signal intensities that hamper the precise characterization of ion peaks.

The solid phase material formed from the polymer of the invention represents a further aspect of the invention.

The solid phase material is suitable for capturing and separating phosphate monoester compounds, the solid phase comprising a binding polymer as defined above.

In the solid phase material, the polymer may be used alone or in combination with other components.

The solid phase is typically in the form of particles and the polymer is a macroporous polymer, the solid phase material may be prepared by a process comprising the steps of crushing and sieving the polymer of the invention.

This process forms a further aspect of the invention.

In other cases, particles may be formed by the methods described above.

There is further provided a separation device comprising the solid phase material. The separation device may comprise a chromatography column, suitably a column for use in liquid chromatography or gas chromatography.

In a further aspect of the invention there is provided a kit for isolating phosphate ester compounds from a mixture comprising one or more such compounds, the kit comprising a solid phase material as defined above and instructions for the use of the material.

The kit may further comprise one or more standards, which may be known phosphoester compounds Suitably, the one or more standards may be provided in known amounts. For example, a kit for the detection of S1P may comprise a known amount of S1P as a standard.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

The invention will now be described in greater detail with reference to the Examples and to the drawings in which.

(b) Extracted ion chromatograms (EIC) of the load, flow-through/wash and eluate fractions as analyzed by liquid chromatography-nanoelectrospray ionization Quadrupole Time of Flight mass spectrometry in either positive (left panel) or negative (right panel) ionization modes.

(c) IMP selectively captures phospho-monoester lipids (Ceramide-1-phosphate, Cer-1-P; sphingosine-1-phosphate, S1P; phosphatidic acid, PA; lysophosphatidic acid, LPA). Lipids with no phosphate (Ceramide, Cer; Glucosyl-Ceramide, Glu-Cer) and those with phosphorous bound in diester configuration (phosphatidylcholine, PC; sphingomyelin, SM; lyso-phosphatidylcholine, LPC; phosphatidylglycerol, PG, and phosphatidylinositol, PI) do not efficiently bind to IMP and are recovered in the flow through and wash fractions instead.

(d) Structure of d17:1 S1P standard before and after derivatization with TMS-diazomethane. The 4Met-S1P derivative (95% of the reaction product) is drawn based on results from high-resolution product ion spectra. (e) Two-step analytical enhancement using IMP enrichment (~2-fold increase in signal intensity, and importantly, removal of matrix interference and TMS derivatization (~30-fold increase in signal intensity) leading to substantially improved detection of long chain base phosphates (LCB-P) with different aliphatic compositions (e.g. the di-ene form of S1P, LCB-P d18:2) in human blood plasma with excellent analytical precision and linearity (Table 2).

Figure 2:
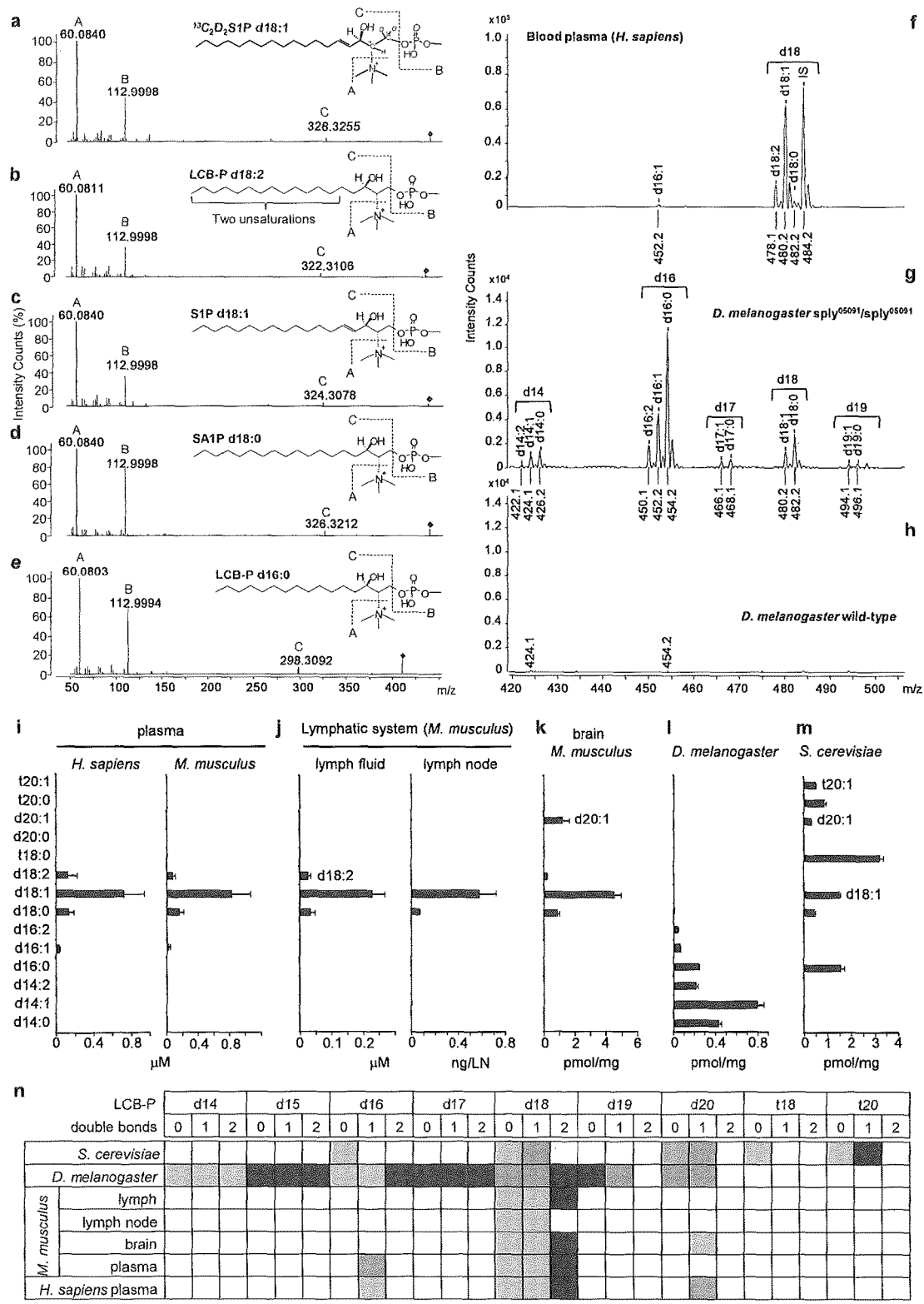

FIG. 2. illustrates the discovery, characterization and quantification of new LCB-P in complex mixtures from diverse biological species (a) Collision-induced dissociation product ion mass spectra (in positive ionisation mode) of TMS-derivatized synthetic stable isotope standard (d18:1 $^{13}C_2D_2$-S1P, m/z 440, diamond symbol) yielded expected ions at m/z 60 (fragment A), m/z 113 (fragment B) and m/z 328 (fragment C). The former two fragments are expected to be invariant for LCB-P with different aliphatic compositions which is indeed the case as shown for corresponding product ion spectra of LCB-P d18:2 (b), LCB-P d18:1 (c) and LCB-P d18:0 (d), all derived from extracts of human blood plasma, and d16:0 (e) from whole fly extract. The C fragment, instead, is characteristic of individual species of LCB-P, thus allowing for identification by targeted tandem mass spectrometry. Targeted mass spectrometric analysis based on scanning for neutral loss of the methylated amine fragment (m/z 60) allows for determination of LCB-P pattern in extracts derived from human plasma (f) and *D. melanogaster* (g and h). Sphingosine-phosphate lyase (sply in *Drosophila*) is the key enzyme in the irreversible degradation of LCB-P. Deletion of this gene in *Drosophila* leads to an accumulation of a multitude of LCB-Ps, many of which have not been described before (g,). Quantification using multiple reaction monitoring of LCB-P in mammalian blood plasma (i) and lymphatic system (j), as well as extracts from model organisms (k-m), led to the discovery of new LCB-Ps (Table 4). (n) LCB-P species detected in this study. Dark blue, new LCB-P not described so far in the literature; light blue, LCB-P not known to exist in the respective biological species/tissue; grey, LCB-P previously described and measured with comparable results in this study (see FIG. 12).

Figure 3:
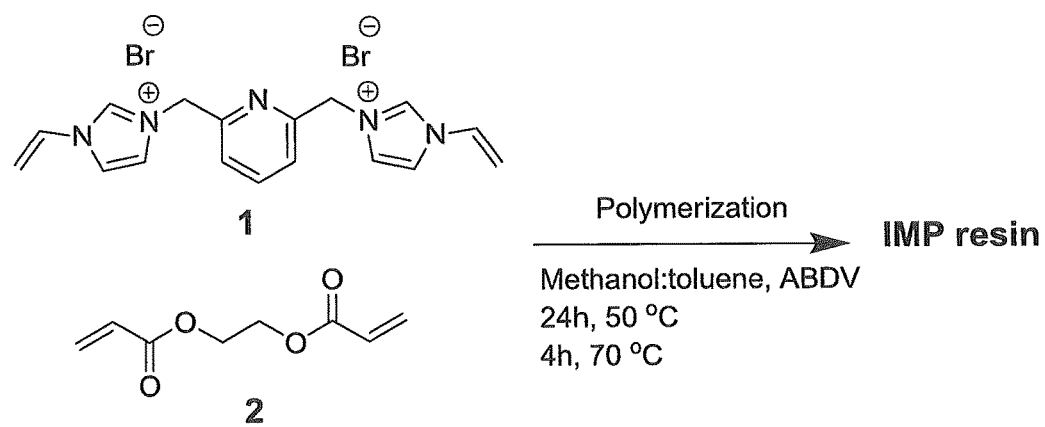

FIG. 3 illustrates the production of an IMP resin.

Figure 4:
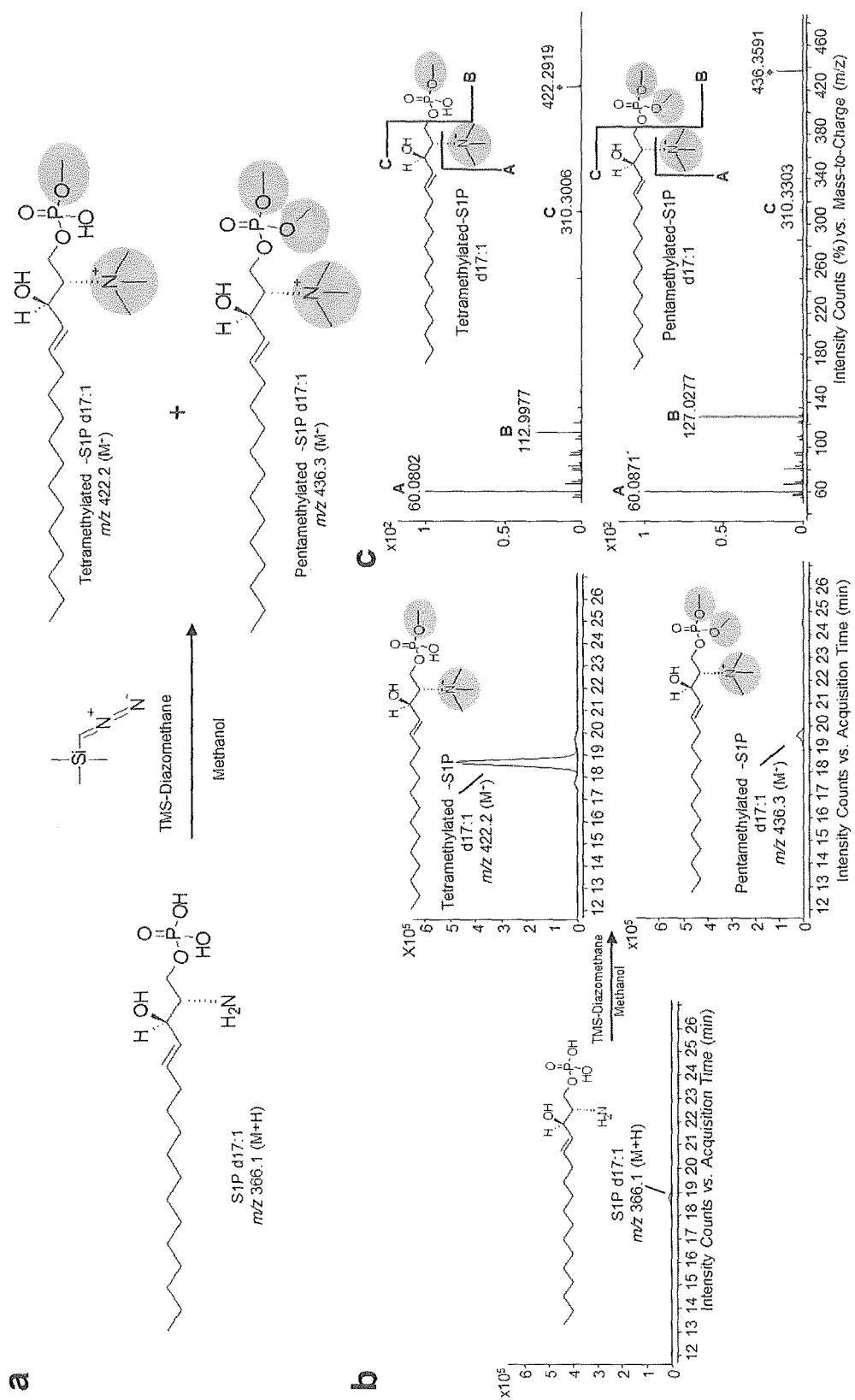

FIG. 4 shows the molecular structures of standard d17:1 S1P before and after derivatization with TMS-diazomethane.

(a) Two different methylated derivatized structures are generated, one containing four methyl groups (top) and one containing five methyl groups (bottom). Methylated moieties are highlighted on red background color.

(b) Chromatographic peaks of S1P d17:1 before (left) and after derivatization (right) recorded with the same LC-MS (positive mode) conditions. After derivatization, the tetra-methylated form represents 95% of the reaction product judged by the relative intensities of the ion chromatograms.

(c) High resolution product ion analysis (using collision induced dissociation) of the tetra-methylated (top) and penta-methylated (bottom) forms. The precursor m/z is labeled with the diamond symbol.

Figure 5:
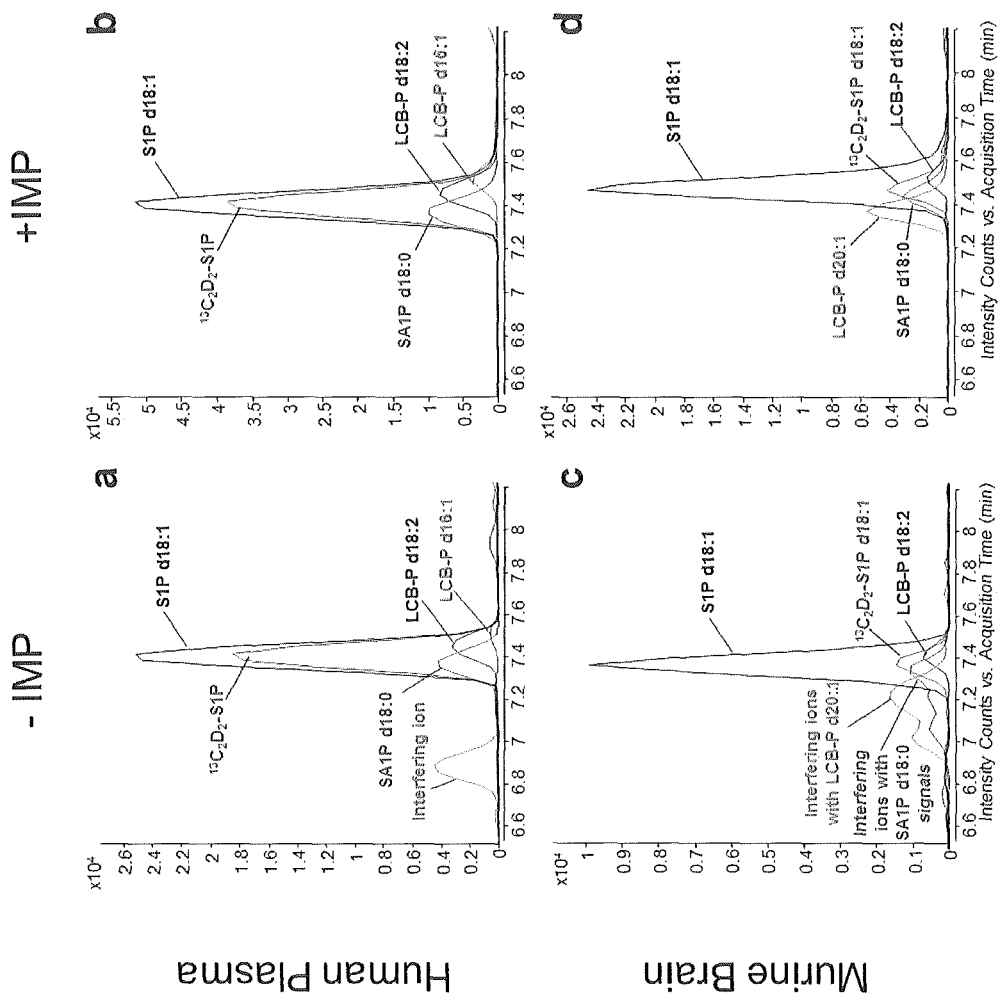

FIG. 5 shows the effect of IMP resin on LCB-Ps detection. Extracted ion chromatograms representing the LCB-Ps identified in human plasma and murine brain, before (a and c) and after (b and d) the IMP enrichment step. Note the different scales in intensities between panels a and c and b and d. IMP enrichment also eliminates co-eluting contaminants (panels a and c) and improves the peak shapes, essential for SA1P and LCB-P d20:1 quantification and the detection of LCB-P d16:1 in plasma.

Figure 6:
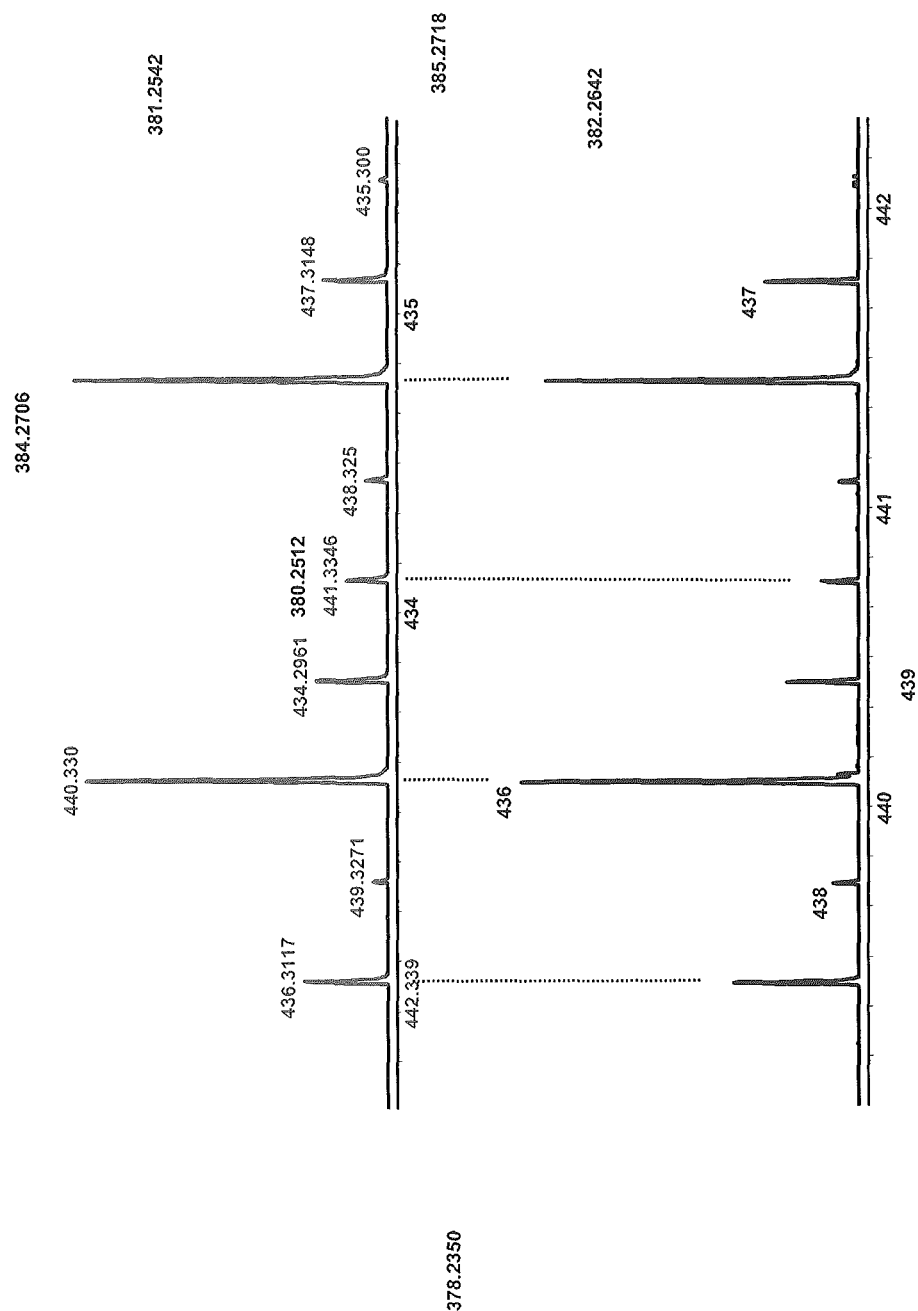

FIG. 6 shows the effect of TMS derivatization on LCB-P species distribution in human plasma. Full scan Quadrupole-Time of Flight mass spectrum of LCB-P species found in the same human plasma sample before (black; lower trace) and after (red; upper trace) derivatization with TMS-diazomethane (both samples were IMP purified). The number of species and their relative abundance is conserved during derivatization.

Figure 7:
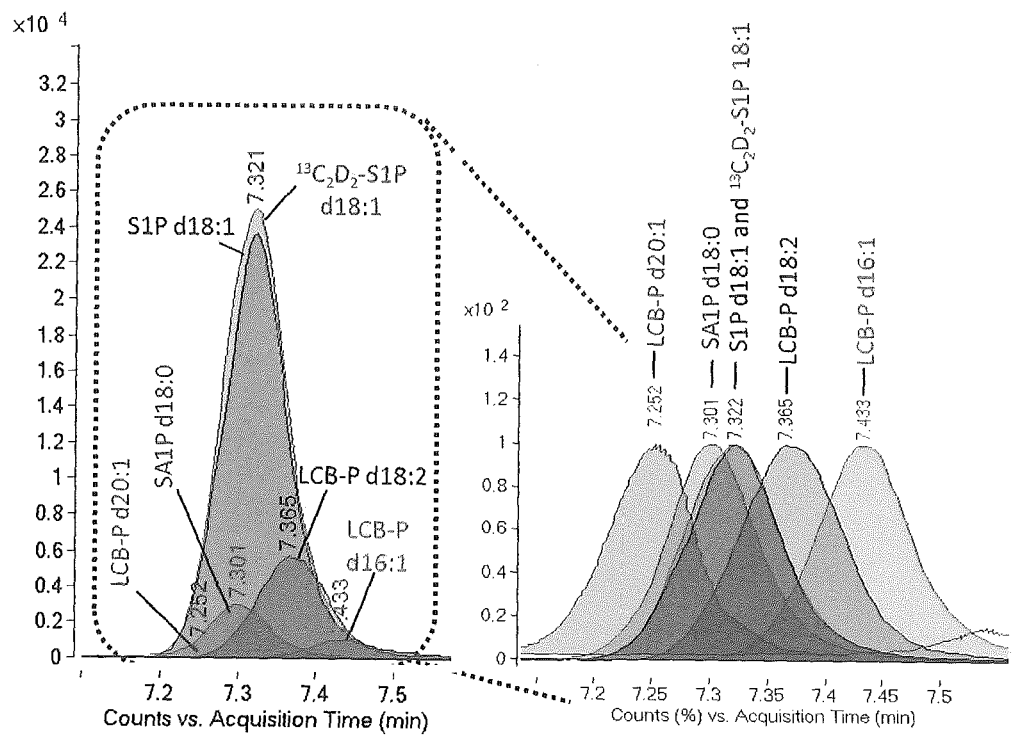

FIG. 7 shows elution peaks recorded by multiple reaction monitoring of derivatized LCB-Ps in human plasma. In the inset, the elution profiles (normalized intensities) are represented, showing a retention time increase with increasing unsaturation and decreasing chain length of the molecules as expected for HILIC chromatography.

Figure 8:
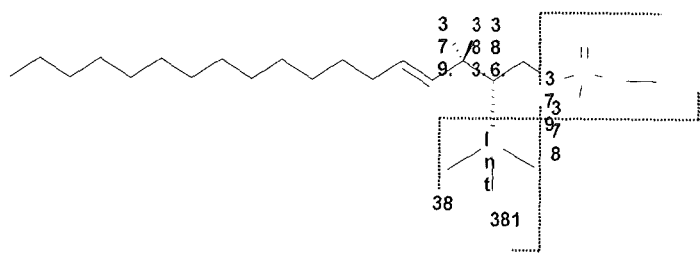

FIG. 8 shows S1P d18:1 for illustration purposes of the different fragments observed during tandem mass spectrometry. Fragments A and B are invariant and common to all LCB-P tested here. Fragment C is LCB-P species specific and recorded as the [M+HCOO]— adduct in negative mode (C**).

Figure 9:
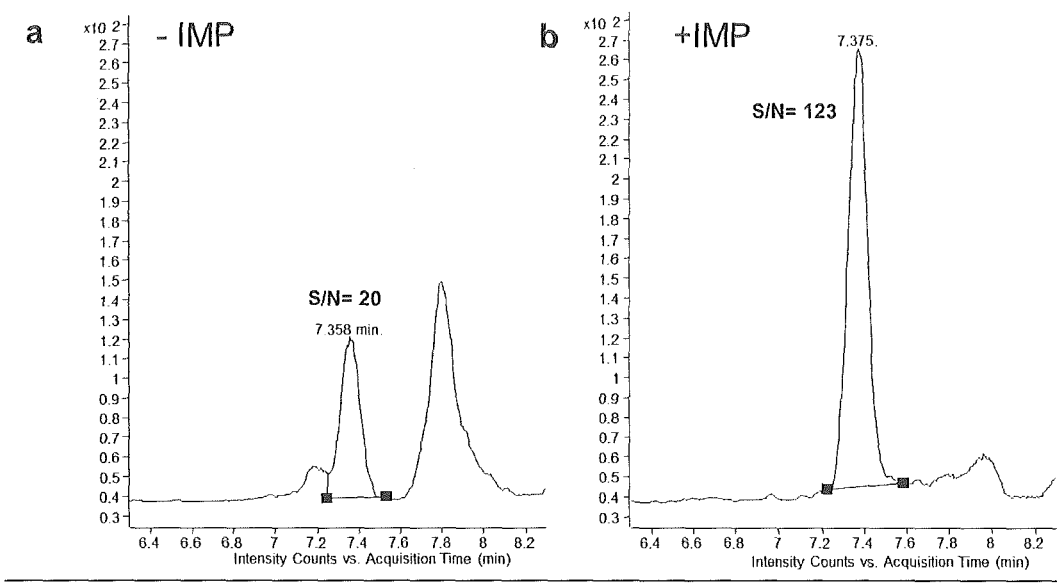

FIG. 9 shows an estimation of the limit of detection (LOD) based on signal to noise ratio (S/N) in plasma before (panel a) and after (panel b) IMP enrichment. Shown are extracted MRM peaks (440.3/60.08, i.e. derivatized 13C$_2$D2 S1P) of 0.3 fmol 13C2D2 S1P spiked into 10 µl human plasma.

Figure 10:
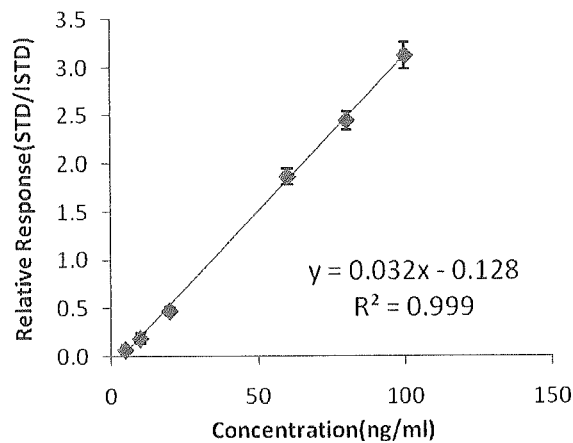
Figure 10:
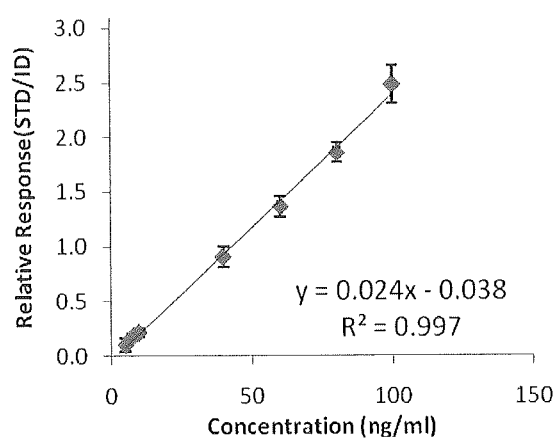

FIG. 10 shows calibration curves for the derivatized S1P standard in human and mouse plasma.

Figure 11:
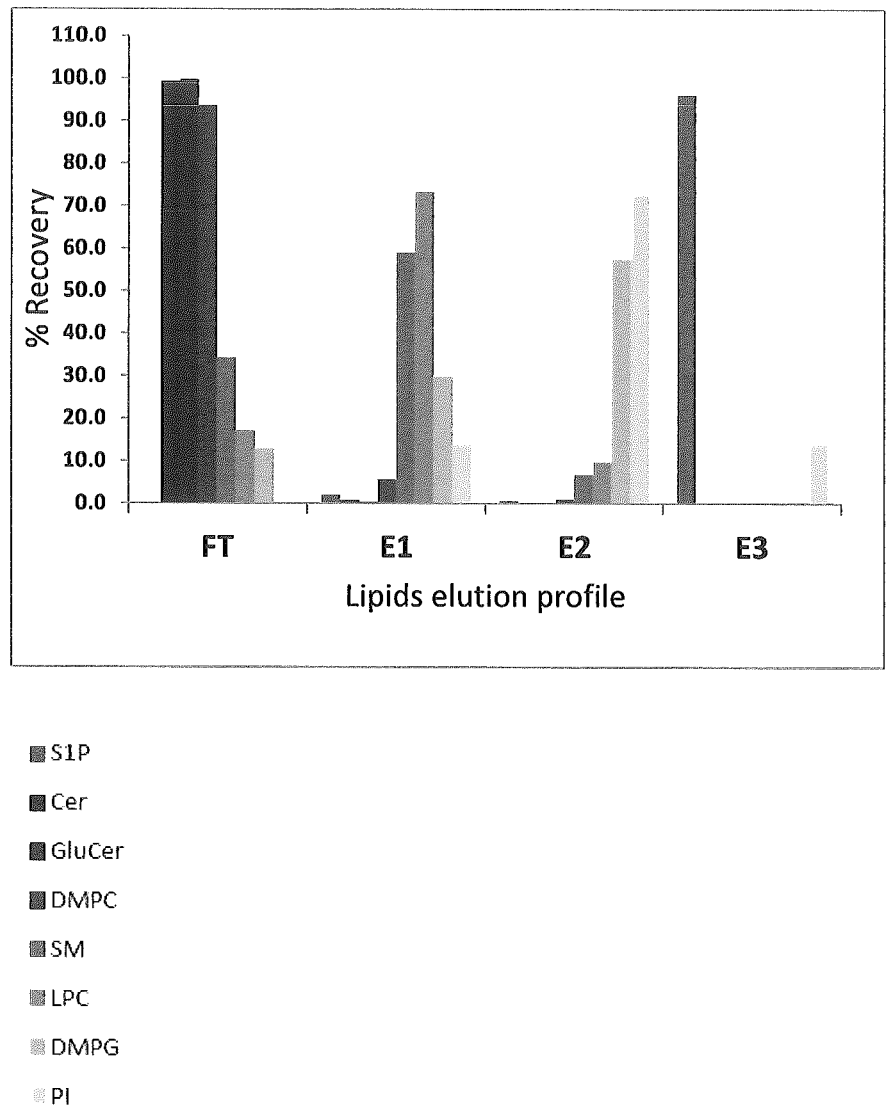

FIG. 11 shows the lipid elution profile for a mixture of compounds including phosphate diester-containing lipids, S1P (a phosphate monoester-containing lipid), other phosphate diesters and non-phosphorylated molecules using the polymer of Example 4a as the stationary phase and a first elution solvent which is isopropanol: methanol 1:1; a second elution solvent which is isopropanol: methanol: triethylamine 49.5:49.5:1; and a third elution solvent which is isopropanol: methanol: 1% trifluoroacetic acid, 49.5:49.5:1.

FIG. 12 shows literature references for LCB-P quantification.

DETAILED DESCRIPTION

Examples

Materials

N-vinylimidazole; 2,6-bis-(bromomethyl) pyridine and ethylene glycol dimethacrylate (EGDMA) were purchased from Sigma Aldrich (St. Louis, Mo.). Dry acetonitrile used for synthesis was purchased from Merck. N,N$^1$-azo-bis-(2, 4-dimethyl) valeronitrile (ABDV) was purchased from Wako. DMSO-d6 was purchased from Deuterio-GmbH (Kastellaun, Germany).

EGDMA was purified by the following procedure prior to use. The received material was washed consecutively with 10% aqueous NaOH, water and brine. After drying over MgSO$_4$, the purified monomer was obtained by distillation under reduced pressure.

All other reagents were used as received.

$^1$H NMR spectra were recorded at 300 MHz unless otherwise mentioned. Elemental microanalyses were performed using a CHN-rapid HERAEUS Analyzer.

All solvents for LC-MS analysis were LC-MS grade and were purchased from Fisher Scientific and Merck Millipore.

Lipid standards: D-erythro-Sphingosine-1-phosphate (S1P d18:1) and isotope labeled standard D-erythro-Sphingosine-1-phosphate ($^{13}$C$_2$D$_2$-S1P,) were purchased from Toronto Research Chemicals, D-erythro-C17-Sphingosine-1-phosphate (S1P d17:1), 1,2-dimyristoyl-sn-glycero-3-phosphocholine (DMPC), 1,2-dimyristoyl-sn-glycero-3-phospho-(1'-rac-glycerol) (DMPG), 1,2-dihexadecanoyl-sn-glycero-3-phosphate (DPPA), 1-heptadecanoyl-2-hydroxy-sn-glycero-3-phosphate (LPA)N-octanoyl-ceramide-1-phosphate (Cer-1P), D-glucosyl-l3-1,1' N-octanoyl-D-erythro-sphingosine (Glu-Cer), N-heptadecanoyl-D-erythro-sphingosine (Cer), N-lauroyl-D-erythro-sphingosylphosphorylcholine (SM) were purchased from Avanti polar lipids (Alabaster, Ala., USA) Dioctanoyl Phosphatidylinositol (PI) was purchased from Echelon Biosciences (USA). Acetic acid, ammonium formate (HPLC grade), formic acid and (Trimethylsilyl) diazomethane solution was purchased from Sigma-Aldrich (St. Louis, Mo.).

Human blood for plasma was obtained from healthy volunteers (NUS-IRB Reference No. 04-115) using EDTA as anticoagulant. Blood samples were centrifuged at 2200×g for 15 min to isolate plasma and frozen at −80° C. within 45 min of blood collection.

Example 1—Synthesis of Monomer 1

The synthesis of Monomer 1 was carried out according to Scheme 1 below.

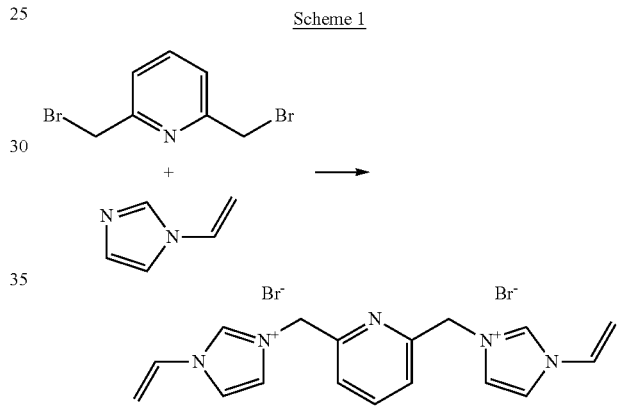

Scheme 1

A solution of 2,6-bis-(bromomethyl) pyridine (Aldrich, 0.5 g, 1.88 mmol) and N-vinylimidazole (Aldrich, 0.35 ml, 3.76 mmol) in acetonitrile (Merck, 25 ml) was refluxed overnight. To prevent polymerisation, a spatula tip of sulphur was added to the reaction mixture. After cooling to room temperature, the solvent was evaporated to dryness under vacuum. The resulting solid was then redissolved in ethanol and precipitated out with the addition of diethyl ether, to afford the desire product (0.71 g) as a solid (83%).

$^1$H NMR (300 MHz, DMSO) δ 5.43-5.47 (m, 2H), 5.64 (s, 4H), 5.98-6.04 (m, 2H), 7.35-7.43 (m, 2H), 7.55-7.57 (d, 2H), 7.87-7.88 (m, 2H), 7.97-8.02 (t, 1H), 8.24-8.25 (t, 2H), 9.67 (s, 2H);

$^{13}$C NMR (75 MHz, DMSO) δ 52.73, 108.92, 118.70, 122.24, 124.11, 128.76, 136.16, 138.82, 153.15.

Calculated C, 45.06%, H, 4.23%, N, 15.45%; found C, 43.26%, H, 4.81%, N, 15.17%.

Example 2—Synthesis of Imidazolium Polymer (IMP) Resin

The synthesis of the IMP resin was carried out as illustrated in Scheme 2.

Scheme 2

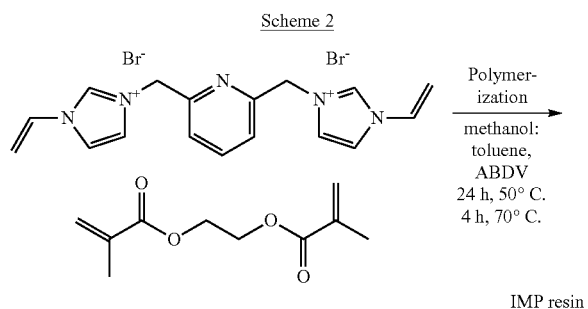

IMP resin

Monomer 1 (134 mg, 0.2975 mmol) and EGDMA (2) (2.25 ml, 11.925 mmol) were mixed into a 20 ml glass vial containing 10 ml of toluene/methanol 1/1. ABDV (25 mg, 0.097 mmol) was added and the solution was degassed for 10 min with $N_2$. The polymerisation tube was sealed and the mixture was kept at 50° C. using a water bath for 24 hours and subsequently at 70° C. for 4 hours. The solid polymer was removed from the glass vial, roughly crushed and Soxhlet extracted with methanol for 48 hours. The crude product was further crushed and sieved to 25-50 μm and sub-25 μm particles. The former fraction was used as sorbent for solid phase extraction.

Example 3—Synthesis of Imidazolium Co Diaryl Urea Polymer (IMUP) Resin

Scheme 3

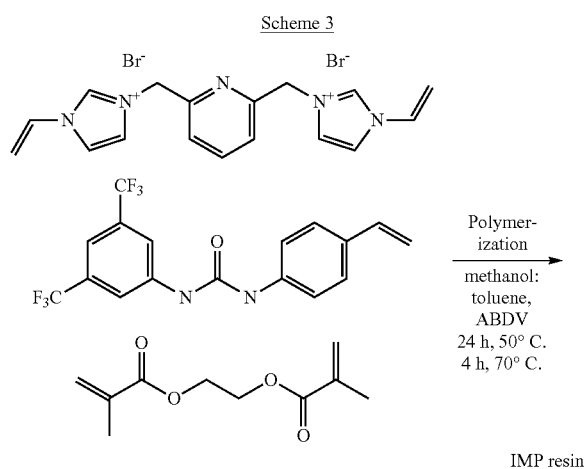

IMP resin

Monomer 1 (54 mg, 0.119 mmol), urea monomer (89 mg, 0.238 mmol) and EGDMA (0.900 ml, 4.77 mmol) were mixed into a 20 ml glass vial containing 4 ml of toluene/methanol 1/1. ABDV (10 mg, 0.0387 mmol) was added and the solution was degassed for 10 min with $N_2$. The polymerisation tube was sealed and the mixture was kept at 50° C. using a water bath for 24 hours and subsequently at 70° C. for 4 hours. The solid polymer was removed from the glass vial, roughly crushed and Soxhlet extracted with methanol for 48 hours. The crude product was further crushed and sieved to 25-50 μm and sub-25 μm particles. The former fraction was used as sorbent for solid phase extraction.

Example 4—Synthesis of Imidazolium Based Imprinted Polymers (i-IMP)

Example 4a: Synthesis of an Imidazolium Based Polymer Imprinted with a Phospholipid Dianion The synthesis of the IMP was carried out as illustrated in Scheme 4 using PL-CL14 template with imdazolium monomer. After subsequent polymerization and removal of template, imprinted polymer was produced.

Scheme 4

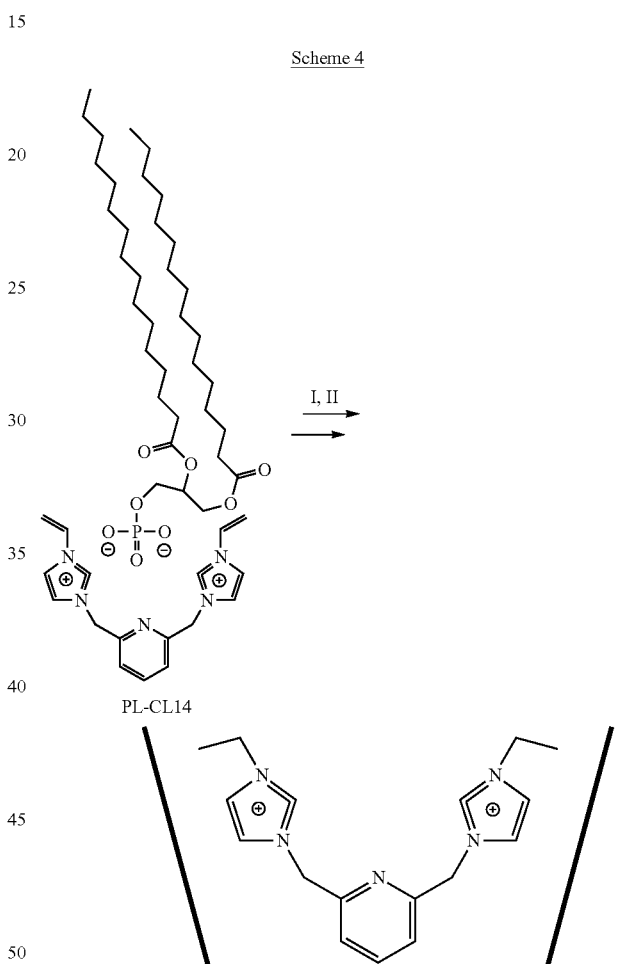

Na salt of PL-C14 (80 mg, 0.119 mmol), 0.120 ml of 1M tetrabutyl ammonium hydroxide (in MeOH), Monomer 1 (54 mg, 0.119 mmol) and EGDMA (0.900 ml, 4.77 mmol) were mixed into a 20 ml glass vial containing 3.880 ml of toluene/methanol 1/1. ABDV (10 mg, 0.0387 mmol) was added and the solution was degassed for 10 min with $N_2$. The polymerisation tube was sealed and the mixture was kept at 50° C. using a water bath for 24 hours and subsequently at 70° C. for 4 hours. The solid imprinted polymer was removed from the glass vial, roughly crushed and Soxhlet extracted with methanol for 48 hours. The crude product was further crushed and sieved to 25-50 μm and sub-25 μm particles. The former fraction was used as sorbent for solid phase extraction.

Example 4b: Synthesis of an Imidazolium Based Polymer Imprinted with a Phospholipid Mono Anion The mono sodium salt of PL-C14 (80 mg, 0.119 mmol), Monomer 1 (54 mg, 0.119 mmol) and EGDMA (0.900 ml, 4.77 mmol) were mixed into a 20 ml glass vial containing 3.880 ml of toluene/methanol 1/1. ABDV (10 mg, 0.0387 mmol) was added and the solution was degassed for 10 min with $N_2$. The polymerisation tube was sealed and the mixture was kept at 50° C. using a water bath for 24 hours and subsequently at 70° C. for 4 hours. The solid imprinted polymer was removed from the glass vial, roughly crushed and Soxhlet extracted with methanol for 48 hours. The crude product was further crushed and sieved to 25-50 μm and sub-25 μm particles. The former fraction was used as sorbent for solid phase extraction.

Example 5—Synthesis of Imidazolium Co Diaryl Urea Based Imprinted Polymer (i-IMUP)

Na salt of PL-C14 (80 mg, 0.119 mmol), 0.120 ml of 1M tetrabutyl ammonium hydroxide (in MeOH), Monomer 1 (54 mg, 0.119 mmol), urea monomer (89 mg, 0.238 mmol) and EGDMA (0.900 ml, 4.77 mmol) were mixed into a 20 ml glass vial containing 3.880 ml of toluene/methanol 1/1. ABDV (10 mg, 0.0387 mmol) was added and the solution was degassed for 10 min with $N_2$. The polymerisation tube was sealed and the mixture was kept at 50° C. using a water bath for 24 hours and subsequently at 70° C. for 4 hours. The solid polymer was removed from the glass vial, roughly crushed and Soxhlet extracted with methanol for 48 hours. The crude product was further crushed and sieved to 25-50 μm and sub-25 μm particles. The former fraction was used as sorbent for solid phase extraction.

Example 6—Synthesis of Monomer 2

The synthesis of Monomer 2 was carried out according to Scheme 5 below.

Scheme 5

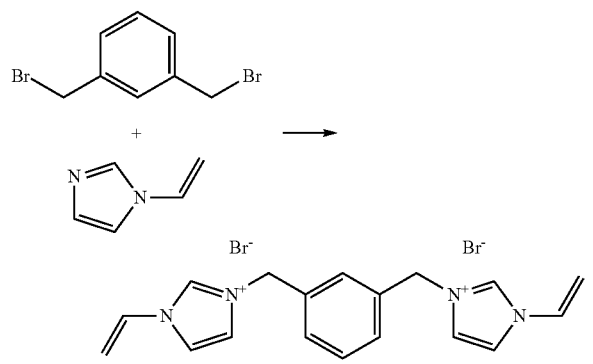

A solution of 1,3-bis(bromomethyl)benzene (Aldrich, 2 g, 7.56 mmol) and vinylimidazole (Aldrich, 1.4 ml, 15.04 mmol) in acetonitrile (Merck, 60 ml) was refluxed overnight. To prevent polymerisation, a spatula tip of sulphur was added to the reaction mixture. After cooling to room temperature, the solvent was evaporated to dryness under vacuum. The resulting solid was then redissolved in ethanol and precipitated out with the addition of diethyl ether, to afford the desire product (2.41 g) as a solid (72%).

$^1$H NMR (400 MHz, DMSO) δ 5.42-5.45 (m, 2H), 5.43, 5.45, 5.45, 5.52 (s, 4H), 5.99-6.04 (m, 2H), 7.33-7.39 (m, 2H), 7.50 (s, 3H), 7.68 (s, 1H), 8.01 (s, 2H), 8.29 (s, 2H), 9.80 (S, 2H);

$^{13}$C NMR (101 MHz, DMSO) δ 51.84, 108.89, 119.45, 123.31, 128.80, 128.86, 128.96, 129.70, 135.10, 135.62.

Calculated C, 47.81%, H, 4.46%, N, 12.39%; found C, 46.08%, H, 4.96%, N, 12.28%.

Example 7—Synthesis of Imidazolium Polymer (IMP2) Resin

The synthesis was carried out according to Scheme 6 below.

Scheme 6

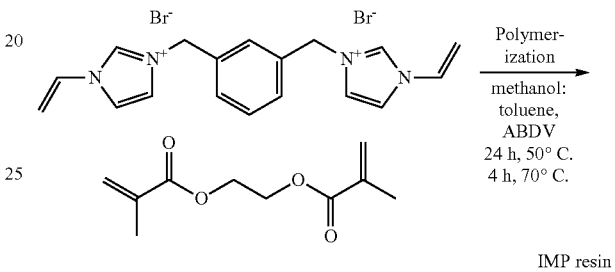

Monomer 2 (134.5 mg, 0.2975 mmol) and EGDMA (2.25 ml, 11.925 mmol) were mixed into a 20 ml glass vial containing 10 ml of toluene/methanol 1/1. ABDV (25 mg, 0.097 mmol) was added and the solution was degassed for 10 min with $N_2$. The polymerisation tube was sealed and the mixture was kept at 50° C. using a water bath for 24 hours and subsequently at 70° C. for 4 hours. The solid polymer was removed from the glass vial, roughly crushed and Soxhlet extracted with methanol for 48 hours. The crude product was further crushed and sieved to 25-50 μm and sub-25 μm particles. The former fraction was used as sorbent for solid phase extraction.

Example 8—Synthesis of Monomer 3

The synthesis of Monomer 3 was carried out according to Scheme 7 below.

Scheme 7

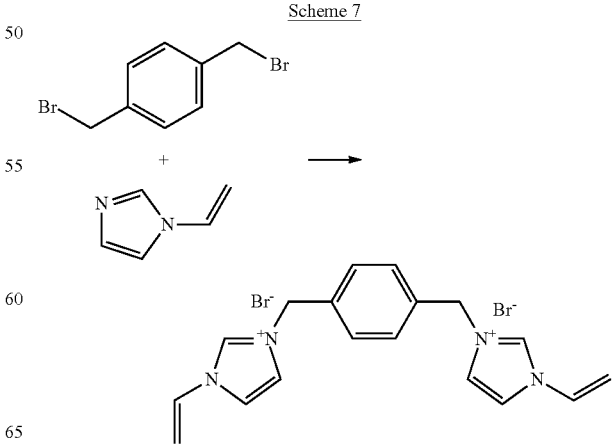

A solution of 1,4-bis(bromomethyl)benzene (Acros, 1.3498 g, 5 mmol) and vinylimidazole (Aldrich, 0.45 ml, 5 mmol) in acetonitrile (Merck, 25 ml) was refluxed over night To prevent polymerisation, a spatula tip of sulphur was added to the reaction mixture. After cooling to room temperature, the solvent was evaporated to dryness under vacuum. The resulting solid was then redissolved in ethanol and precipitated out with the addition of diethyl ether, to afford the desire product 40% as a solid.

$^1$H NMR (300 MHz, DMSO) δ 5.39-5.42 (d, 2H), 5.53 (s, 4H), 6.00-6.06 (m, 2H), 7.33-7.42 (m, 2H), 7.58 (s, 4H), 8.04 (s, 2H), 8.31 (s, 2H), 10.03 (s, 2H); $^{13}$C NMR (75 MHz, DMSO) δ 51.65, 108.78, 119.50, 123.27, 128.92, 129.26, 135.11, 135.73.

Calculated C, 59, 51%, H, 5.55%, N, 15.42%; found C, 53.27%, H, 6.65%, N, 13.82%.

Example 9—Synthesis of Imidazolium Polymer (IMP3) Resin

The synthesis of the IMP3 resin was carried out as illustrated in Scheme 8.

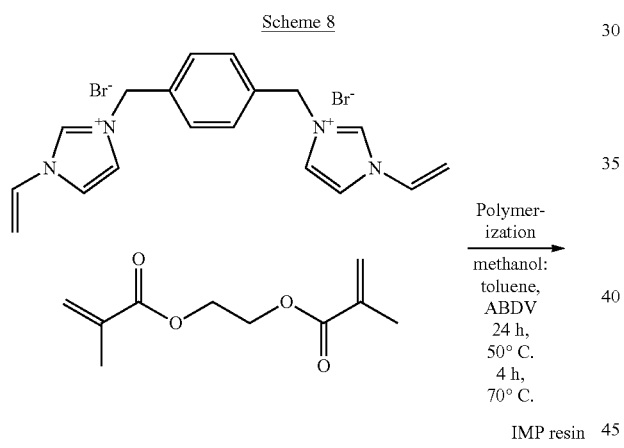

Monomer 3 (134 mg, 0.2975 mmol) and EGDMA (2) (2.25 ml, 11.925 mmol) were mixed into a 20 ml glass vial containing 10 ml of toluene/methanol 1/1. ABDV (25 mg, 0.097 mmol) was added and the solution was degassed for 10 min with N$_2$. The polymerisation tube was sealed and the mixture was kept at 50° C. using a water bath for 24 hours and subsequently at 70° C. for 4 hours. The solid polymer was removed from the glass vial, roughly crushed and Soxhlet extracted with methanol for 48 hours. The crude product was further crushed and sieved to 25-50 μm and sub-25 μm particles. The former fraction was used as sorbent for solid phase extraction.

Example 10—Synthesis of Monomer 4

The synthesis of Monomer 4 was carried out according to Scheme 9 below.

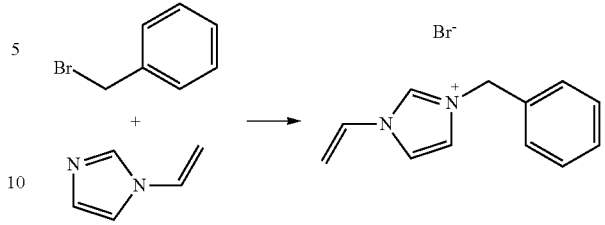

A solution of bromomethylbenzene (Acros, 0.86, 5 mmol) and vinylimidazole (Aldrich, 0.45 ml, 5 mmol) in acetonitrile (Merck, 25 ml) was refluxed over night. To prevent polymerisation, a spatula tip of sulphur was added to the reaction mixture. After cooling to room temperature, the solvent was evaporated to dryness under vacuum. The resulting solid was then redissolved in ethanol and precipitated out with the addition of diethyl ether, to afford the desire product (1 g) as a solid (81%).

$^1$H-NMR (CDCl$_3$, 500 MHz) δ: 5.35 (d, 1H), 5.66 (s, 2H), 5.97 (dd, 1H), 7.26-7.37 (m, 4H), 7.49-7.53 (m, 3H), 7.77 (s, 1H), 11.10 (s, 1H).

$^{13}$C NMR (CD$_3$OD, 101 MHz) δ 54.43, 99.93, 106.3, 110.05, 120.92, 124.28, 127.24, 129.83, 130.49, 134.76.

Example 11—Synthesis of Monomer 5

The synthesis of Monomer 5 was carried out according to Scheme 10 below.

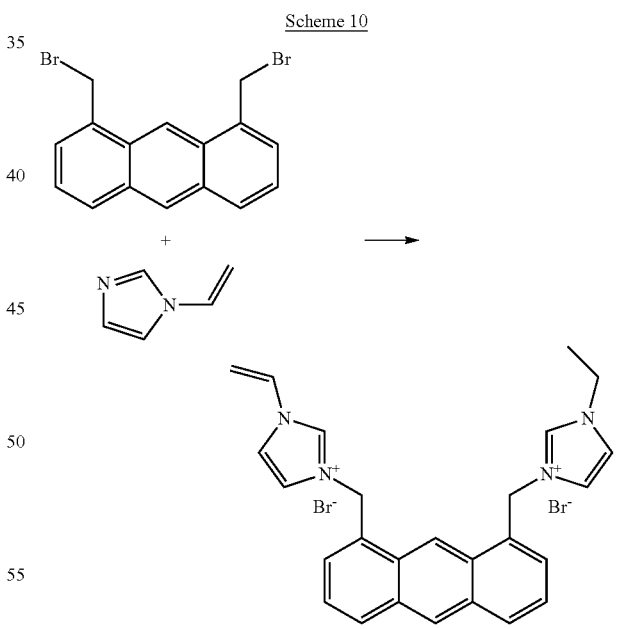

A solution of 1,8 bis (bromomethyl) anthracene (Aldrich 5 mmol) and vinylimidazole (Aldrich, 5 mmol) in acetonitrile (Merck, 25 ml) was refluxed over night. To prevent polymerisation, a spatula tip of sulphur was added to the reaction mixture. After cooling to room temperature, the solvent was evaporated to dryness under vacuum. The resulting solid was then redissolved in ethanol and precipitated out with the addition of diethyl ether, to afford the desire product as a solid.

Example 12 Synthesis of an Imidazolium Based Polymer from Monomer 5 Imprinted with a Phospholipid Dianion Na salt of PL-CL14 (Scheme 4) (80 mg, 0.119 mmol), 0.120 ml of 1M tetrabutyl ammonium hydroxide (in MeOH), Monomer 5 (67 mg, 0.119 mmol) and EGDMA (0.900 ml, 4.77 mmol) were mixed into a 20 ml glass vial containing 3.880 ml of toluene/methanol 1/1. ABDV (10 mg, 0.0387 mmol) was added and the solution was degassed for 10 min with $N_2$. The polymerisation tube was sealed and the mixture was kept at 50° C. using a water bath for 24 hours and subsequently at 70° C. for 4 hours. The solid imprinted polymer was removed from the glass vial, roughly crushed and Soxhlet extracted with methanol for 48 hours. The crude product was further crushed and sieved to 25-50 µm and sub-25 µm particles. The former fraction was used as sorbent for solid phase extraction.

Example 13

Liquid Chromatography (LC) and Mass Spectrometry (MS)

All LC-MS/MS experiments were performed using Agilent 1200 series HPLC-Chip systems connected to Agilent 6540 or 6550 Q-TOF and to Agilent 6490 QQQ mass spectrometers. Two different types of chip were used for Reverse Phase (only for initial studies on pure standards) and HILIC separations:

(1) The Reverse Phase Ultra High capacity Chip included a 500 nl enrichment column (5 µm particle size, 80 Å pore size) and a 75 µm×150 mm C18 analytical column (Agilent Technologies Corp., Santa Clara Calif.). The Agilent 1200 series HPLC used a capillary pump for sample injection onto the Enrichment column and a Nano pump for separation. Solvents used for the Reverse Phase LC: 5% water in 95% methanol with 5 mM ammonium formate and 0.1% formic acid (solvent A), 50% methanol in 50% isopropanol with 5 mM ammonium formate and 0.1% formic acid (solvent B). Analytes were eluted with the following gradient: 5% B to 20% B from 0 to 2 min, 60% B from 2 to 8 mins, 100% B from 8 to 18 min, 100% B from 18 to 23 min, 5% B from 23.1 to 33 min. The chip cube was operated with back flush mode and samples were injected through the enrichment column at 4 µl/min. The valve was switched after 1.5 min to place the enrichment column in line with analytical column at a flow rate of 400 nl/min. The Agilent 6540 (or 6550) quadrupole time-of-flight (QTOF) mass spectrometer was operated in positive ion mode; electrospray voltage was set to 1600 V (Vcap), temperature 300° C., drying gas 4 (or 12) l/min, fragmentor voltage 150 V. The instrument was operated in targeted MS/MS mode with MS acquisition rate of 1 spectra/sec and MS/MS acquisition rate of 2.0 spectra/sec. All the samples were resuspended in 50 or 100 µl of mobile phase A before injecting 1 µl of sample for LC-MS analysis.

(2) A customised HILIC-chip containing Amide-80 stationary phase (Tosoh Bioscience, LLC. Montgomeryville, Pa., 5 µm particle size, 80 Å pore size) was also prepared, including a 160 nl trapping column and a 75 µm×150 mm analytical column (Agilent Technologies Corp., Santa Clara Calif.).

Solvents used for HILIC HPLC: 50% acetonitrile in water containing 25 mM ammonium formate pH 4.6 (solvent A), 95% acetonitrile containing 25 mM ammonium formate pH 4.6. The pH value was adjusted with formic acid.

Analytes were eluted with the following gradient: 100% B from 0 to 1.5 min, 40% B from 1.5 to 8.5 min, 30% B from 8.5 to 10.5 min, 0% B from 11.5 to 13.0 min, 100% B from 13.1 to 19 min.

The chip cube was operated with back flush mode and samples were injected through the enrichment column at 4 µl/min. The valve was switched 1.5 min after injection to place the enrichment column in line with the analytical column at a flow rate of 400 nl/min. The Agilent 6540 (or 6550) instrument was operated with the same parameters described previously, except for the gas temperature kept at 185° C. and Vcap set at 1580 V. Spectra were acquired in targeted MS/MS mode with MS acquisition rate of 2 spectra/sec and MS/MS acquisition rate of 2 spectra/sec.

For the validation of the method, murine and human plasma samples were spiked with known amounts of standard S1P d18:1 and ISTD (S1P-$^{13}C_2D_2$) in the concentrations reported below. The Agilent 6490 triple quadrupole (QQQ) mass spectrometer was operated in positive mode for MRM (see Table 1 for instrument parameters and MRM transitions) and negative mode for neutral loss (NL) scan mode (for NL of 60 m/z, electrospray voltage was set to 1580 V (Vcap), temperature 185° C., drying gas 12 l/min and collision energy of 25 V). In positive ion MRM mode, two product ions were monitored after CID of the LCB-P precursors.

TABLE 1

Multiple reaction monitoring (MRM) parameters for LCB-P Product ion m/z 60.08 was used as Quantifier and Product ion m/z 113 was used as Qualifier for accurate identification and quantification of LCB-P species

| Compound Group | Compound Name | Precursor Ion | Product ion |
|---|---|---|---|
| t20 | LCB-P t20:0 | 482.3 | 113.0 |
|  |  | 482.3 | 60.1 |
|  | LCB-P t20:1 | 480.3 | 113.0 |
|  |  | 480.3 | 60.1 |
| d20 | LCB-P d20:0 | 466.3 | 113.0 |
|  |  | 466.3 | 60.1 |
|  | LCB-P d20:1 | 464.3 | 113.0 |
|  |  | 464.3 | 60.1 |
|  | LCB-P d20:2 | 462.3 | 113.0 |
|  |  | 462.3 | 60.1 |
| d19 | LCB-P d19:0 | 452.3 | 113.0 |
|  |  | 452.3 | 60.1 |
|  | LCB-P d19:1 | 450.3 | 113.0 |
|  |  | 450.3 | 60.1 |
|  | LCB-P d19:2 | 448.3 | 113.0 |
|  |  | 448.3 | 60.1 |
| t18 | LCB-P t18:0 | 454.3 | 113.0 |
|  |  | 454.3 | 60.1 |
|  | LCB-P t18:1 | 452.3 | 113.0 |
|  |  | 452.3 | 60.1 |
| d18 | $^{13}C_2D_2$-S1P d18:1 | 440.3 | 113.0 |
|  |  | 440.3 | 60.1 |
|  | SA1P d18:0 | 438.3 | 113.0 |
|  |  | 438.3 | 60.1 |
|  | S1P d18:1 | 436.3 | 113.0 |
|  |  | 436.3 | 60.1 |
|  | LCB-P d18:2 | 434.3 | 113.0 |
|  |  | 434.3 | 60.1 |
| d17 | LCB-P d17:0 | 424.3 | 113.0 |
|  |  | 424.3 | 60.1 |
|  | LCB-P d17:1 | 422.3 | 113.0 |
|  |  | 422.3 | 60.1 |
|  | LCB-P d17:2 | 420.3 | 113.0 |
|  |  | 420.3 | 60.1 |
| d16 | LCB-P d16:0 | 410.3 | 113.0 |
|  |  | 410.3 | 60.1 |
|  | LCB-P d16:1 | 408.3 | 113.0 |
|  |  | 408.3 | 60.1 |
|  | LCB-P d16:2 | 406.3 | 113.0 |
|  |  | 406.3 | 60.1 |

TABLE 1-continued

Multiple reaction monitoring (MRM) parameters for LCB-P Product ion m/z 60.08 was used as Quantifier and Product ion m/z 113 was used as Qualifier for accurate identification and quantification of LCB-P species

| Compound Group | Compound Name | Precursor Ion | Product ion |
|---|---|---|---|
| d15 | LCB-P d15:0 | 396.3 | 113.0 |
|  |  | 396.3 | 60.1 |
|  | LCB-P d15:1 | 394.3 | 113.0 |
|  |  | 394.3 | 60.1 |
|  | LCB-P d15:2 | 392.3 | 113.0 |
|  |  | 392.3 | 60.1 |
| d14 | LCB-P d14:0 | 382.3 | 113.0 |
|  |  | 382.3 | 60.1 |
|  | LCB-P d14:1 | 380.3 | 113.0 |
|  |  | 380.3 | 60.1 |
|  | LCB-P d14:2 | 378.3 | 113.0 |
|  |  | 378.3 | 60.1 |

| | |
|---|---|
| Dwell time (msec) | 20 |
| Fragmentor | 380 |
| Collision Energy | 25 |
| Cell Accelerator voltage | 7 |
| Polarity | Positive |

Quantification peak areas of LCB-P compared to peak area of internal standard (IS)

M/z 60 was used as a 'quantifier' (due to its high intensity) and m/z 113 was used as a 'qualifier' (except in the case of phytosphingosines where m/z 113 was used as the quantifier). These ions were present after fragmentation of all LCB-P species. The qualifier at m/z 113 represents the mono-methylated phosphate and was used to discriminate between penta-methylated species generated by the derivatization reaction. Quantification was performed according to the internal standard method, comparing peak areas of the sample to the internal standard. The method shows linearity in the physiological range that has been reported for S1P (Table 2 and FIG. 10). All the samples were resuspended in 50 or 100 µl of mobile phase B before injecting 1 µl of sample for LC-MS analysis.

TABLE 2

Intraday/interday precision and accuracy for S1P in human plasma

| Conc (ng/ml) | n | Intraday | | | Interday | | |
|---|---|---|---|---|---|---|---|
| | | Mean ± SD | Accuracy (%) | Precision (%) | Mean ± SD | Accuracy (%) | Precision (%) |
| Low QC | 5 | 5 | 5.26 ± 0.26 | 105.29 | 5.18 | 4.95 ± 0.25 | 99.04 | 13.14 |
| Middle QC | 40 | 4 | 39.64 ± 0.96 | 99.12 | 2.4 | 39.72 ± 1.3 | 100.35 | 3.59 |
| High QC | 80 | 5 | 80.92 ± 2.43 | 101.16 | 3.04 | 82.54 ± 4.66 | 104.58 | 5.92 |

Preparation of Standards

Main stock solutions of standards were diluted in methanol to a final concentration of 0.5 mg/ml for d18:1 S1P, $^{13}C_2D_2$-S1P (Internal Standard, IS) and d17:1 S1P. The stock solutions were further diluted in a concentration range of 50-1000 ng/ml for S1P (d18:1) for validation experiments, while the internal standard stock was kept at a concentration of 200 ng/ml or 400 ng/ml.

Sample Extraction from Human Plasma

All healthy human plasma samples were collected from a representative cohort of the Singaporean population in accordance to ethical guidelines and protocols approved by the National Health Group Institutional Review Board, Singapore. All participants who were approached and agreed to participate in this study were required to provide written consent by signing on consent forms. Participants were required to fast overnight for at least 8 hours and samples were collected between 8 to 10 am to minimize changes in metabolite profile due to circadian rhythm. 10 ml of whole blood samples were obtained in BD Vacutainer® plastic plasma tubes with EDTA as anti-coagulant by venipuncture. Plasma was processed by spinning 10 ml of fresh blood collected at 2,200 g for 15 mins at 4° C. using a swing-out bucket rotor centrifuge. Subsequently the plasma was transferred to 5 ml cryovials (Practical Mediscience). The plasma was frozen at −80° C. For LCB-P extraction 10 µl plasma were mixed with 10 µl IS and 90 µl methanol. The solution was shaken on a thermomixer for 20 min at 4° C. and centrifuged for 10 mins at 14,000 rpm. The supernatant could then be diluted in isopropanol for loading onto the IMP resin or directly derivatised for analysis.

Sample Extraction from Murine Plasma and Lymph

Male Wild Type C57 BL/6 (WT) mice were obtained from the Jackson Laboratory (Bar Harbor, Me.). All mice were maintained on a chow diet (18% protein and >5% fat, Harlan Teklad, Madison, Wis.) post wean until 6 weeks of age. Diet was then switched to a Western-type (21.2% fat and 0.2% cholesterol, Harlan Teklad) until mice were sacrificed at 22-28 weeks of age. Mice were maintained under specific pathogen-free conditions with free access to food and water in the Animal Housing Unit of the National University of Singapore. All studies were performed under protocols approved by the Institutional Animal Care and Use Committee (IACUC) of the National University of Singapore. Blood was drawn from the mice via cardiac puncture immediately after sacrifice and mixed with 50 µl of 100 mM EDTA. The blood-EDTA mixture was then centrifuged at 14000 g, for 10 minutes at 4° C. and the plasma was obtained from the supernatant for subsequent S1P extraction. Special care was taken to minimize red blood cells and platelets lysis throughout the whole process, avoiding aspiration of blood through fine needles. All mice were fasted overnight prior to lymph collection to clear dietary lipids from the lymph fluid. 25 µl of lymph fluid were crenulated from the cysterna chili with the use of extended length gel-loading pipette tips (Neptune Scientific) and collected into a new Eppendorf tube. The lymph samples were centrifuged at 14,000 g for 10 minutes at 4° C. and the supernatant was obtained for subsequent S1P extraction.

10 µl plasma (5 µl for Lymph) were mixed with 10 µl IS (5 µl IS for lymph) and 90 µl methanol. Samples were then treated in the same way as for human plasma.

Method Validation
Recovery Studies.

The extraction recovery of S1P was determined by spiking the Internal Standard (IS)$^{13}C_2D_2$-S1P in the plasma samples at two different concentrations (40 and 80 ng/ml, n=3) before lipid extraction. The recoveries of IS were determined from the ratio of the mean peak area of the extracted samples to the mean peak area of samples where the internal standard was spiked after extraction. The recovery for IS at concentrations of 40 ng/ml and 80 ng/ml was 80.1±9.6% and 87.9±9.5%, respectively, in human plasma and 82.1±5.4% and 97.4±2.5% in mouse plasma.

Calibration Curves.

Calibration curves (FIG. 10) were constructed using the standard addition method using a double blank (extracted plasma samples without IS), a blank (extracted plasma sample with IS) and 8 standards containing 5, 7.5, 10, 20, 40, 60, 80, 100 ng/ml concentration of S1P (d18:1) spiked in plasma together with IS (40 ng/ml). The results were fitted by a linear equation from 5 to 100 ng/ml and the resulting mean regression equations for S1P in human plasma (y=0.032x−0.128) and in mouse plasma (y=0.024x−0.038) showed $R^2$ values of 0.9993 and 0.9972 respectively (Table 2).

Precision and Accuracy.

Intra-day/inter-day precision and accuracy were determined by analyzing quality control samples (QC) consisting of human plasma spiked with standard S1P (d18:1) at three different concentration levels, Low-QC (5 ng/ml), Middle-QC (40 ng/ml) and High-QC (80 ng/ml), and a fixed IS concentration of 40 ng/ml. Five replicates for each control were analysed while a plasma lipid extract spiked with IS was used as blank, to subtract the area of the endogenous S1P when calculating precision and accuracy.

Sample Extraction from Murine Tissues

Lymph nodes (1 lymph node/sample) and brain samples (2.5 or 5 mg) from individual mice were resuspended in 190 µl of methanol+10 µl of IS. Samples were sonicated in water bath at 4° C. for 30 min. After centrifuging at 4° C. for 10 min at 14,000 rpm, the supernatant was collected for enrichment onto IMP resin.

Sample Extraction from *D. melanogaster*

Adult flies (up to 2 days old), fed on standard Bloomington semi-defined *Drosophila* medium, of the genotypes+/+ (homozygous w$^{1118}$), sply$^{05091}$/sply$^{05091}$ homozygotes and sply$^{05091}$/+heterozygotes (resulting from a cross between sply$^{05091}$ and w$^{1118}$) were collected, flash frozen in liquid nitrogen, and stored at −80 C for up to one week before lipid extraction, Extractions of LCB-Ps were done in triplicate. For each experiment 5 flies were weighed and, after addition of 5 µl IS (40 ng/ml), homogenised in 500 µl methanol by using a pellet pestle (Sigma). After addition of 500 µl methanol, the samples were sonicated for 1 h at 4° C. After centrifugation at 14000 rpm, 4° C., for 10 min, supernatant was collected and dried in speedvac. Samples were resuspended in 100 µl of methanol prior enrichment onto IMP resin and derivatization.

Sample Extraction from *S. cerevisiae*

Pre-cultures of *S. cerevisiae* (W303) were grown in YPD medium (BD) for 24 h at 30° C. Then YPD was inoculated to a starting OD$_{600}$ of 0.1 and cells were grown at 30° C. until they reached OD 1. Cells were then harvested and lyophilized. 2.5 mg of lyophilized yeast were resuspended in 500 µl methanol and after addition of 5 µl IS (400 ng/ml), homogenised with glass beads by vortexing for 2 min. After addition of 500 µl methanol, the samples were sonicated for 1 h at 4° C. After centrifugation at 14,000 rpm, 4° C., for 10 min, supernatant was collected and dried in speedvac. Samples were resuspended in 100 µl of methanol prior enrichment onto IMP resin and derivatization.

Example 14—Selective Binding and Elution of S1P

Different protocols were optimized for selective capture of S1P and related species (as described later) with different solvents for conditioning, loading, washing, eluting and regenerating the resin in an offline format. To do so, 10 (for plasma and lymph) and 20 (for tissues) mg of the IMP resin were dry packed in an empty 96 well plate (Agilent) with polypropylene filters at both bottom and top of the resin.

To investigate the selectivity of the IMP resin for LCB-Ps, standard lipids were loaded and eluted in different conditions. The effect of various percentages of basic and acidic solutions was investigated (data not shown). Best selectivity and recovery were obtained when loading the resuspended sample in 1 ml isopropanol and washing the resin sequentially with 1 ml isopropanol, 1 ml isopropanol/methanol (50/50). Elution was obtained with 2×0.8 ml chloroform/methanol/1% trifluoroacetic acid (49.5/49.5/1). This enrichment protocol was applied to all the analysed biological samples.

The IMP resin wells can be reused after regenerating with 3×1 ml methanol/acetic acid/water (60/30/10) and equilibrating with 3×1 ml loading solution.

Derivatization Step

The obtained fractions were dried and reconstituted in 100 µl of methanol. 10 µl of TMS-Diazomethane (2M in hexane) were added and the sample incubated for 20 min at room temperature under gentle mixing at 750 rpm. The reaction was stopped by adding 1 µl of acetic acid. The derivatized samples were dried in speedvac and reconstituted in 100 µl of mobile phase before injecting into the LC-MS system.

To test the recovery rate from the IMP resin with the reported enrichment protocol, a brain tissue extract obtained as described above was spiked with standard DMPC (250 ng), DMPG (100 ng), Glu-Cer (100 ng), SM (50 ng), LPC (50 ng), Cer (50 ng), C8-PI (15 ng), S1P ISTD (4 ng), DPPA (50 ng), Cer-1P (50 ng), LPA (50 ng) before homogenisation and loaded onto the IMP resin in 1 ml loading solution. The lipid content of the different fractions (flow through+wash and eluate) was measured by LC-MS before (for phosphate diesters and non-phosphorylated species detection) and after (for monoesters) derivatization with TMS. Recovery in flow through+wash and eluate was estimated as % of the lipids present in the loaded fraction.

Figure 1:
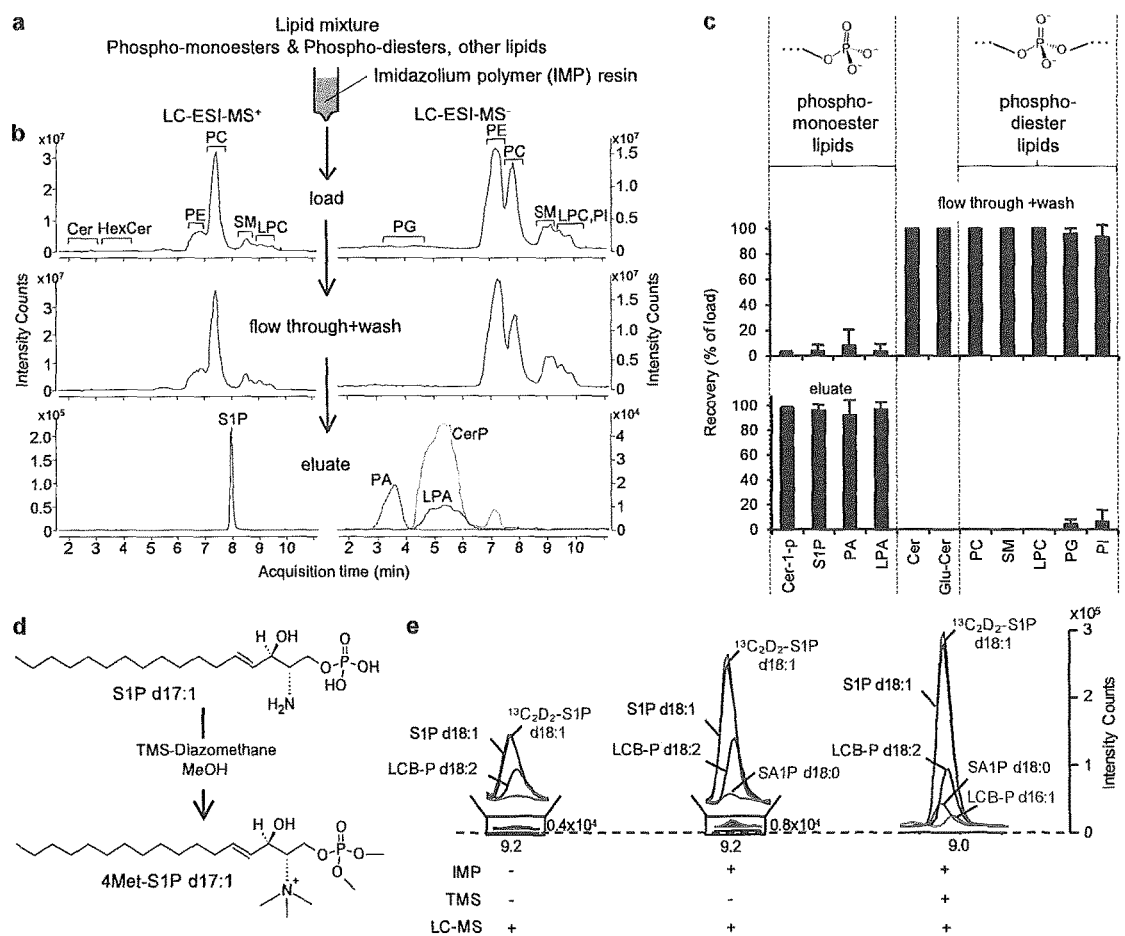
FIG. 1. illustrates substantially improved detection of LCB-P via an analytical workflow using phospho-monoester capture and derivatization (a) Methanol extracts from different types of starting materials were loaded onto an imidazolium polymer (IMP) after protein precipitation.

When fragmented by collision-induced dissociation (CID), derivatized d18:1 13C2D2-S1P standard (m/z 440) yielded three product ions, denoted ions A-C. Originating from the methylated amine group (fragment A at m/z 60; FIG. 2a) and methyl-phosphate (fragment B at m/z 113), both A and B ions are expected to be invariant for different LCB-Ps compared with ion C (m/z 328), which originated from the aliphatic portion. Indeed, when LCB-Ps from plasma were analyzed, the C fragment yielded m/z values as predicted for d18:2 (FIG. 1b), d18:1 (FIG. 2c), d18:0 (FIG. 2d) and d16:0 for a lipid extract from fly (FIG. 2e, FIG. 6).

The product ion analysis of derivatised LCB-Ps was obtained using collision induced dissociation (CID). FIG. 8 shows S1P d18:1 for illustration purposes of the different fragments observed during tandem mass spectrometry. Fragments A and B are invariant and common to all LCB-P tested here. Fragment C is LCB-P species specific and recorded as the [M+HCOO]— adduct in negative mode (C**).

Tables 3a (positive ion mode) and 3b (negative ion mode) are a summary of the main fragments generated by CID fragmentation in both positive and negative mode for each LCB-P molecular species reported in this study (See FIG. 8). All data were collected using Quadrupole Time of Flight (QToF) mass spectrometry except # which were acquired on a triple quadrupole mass spectrometer.

TABLE 3a

| LCB-P | | m/z precursor | Product ions (m/z) | | |
|---|---|---|---|---|---|
| | | | A | B | C* |
| d14 | 0 | 382.270 | 60.080 | 112.999 | 270.277 |
| | 1 | 380.254 | 60.080 | 112.999 | 268.261 |
| | 2 | 378.238 | 60.080 | 112.999 | 266.247 |
| d15 | 0 | 396.284 | 60.080 | 112.998 | 284.292 |
| | 1 | 394.269 | 60.079 | 112.999 | 282.275 |
| | 2 | 392.255 | 60.080 | nd | nd |
| d16 | 0 | 410.301 | 60.083 | 112.999 | 298.309 |
| | 1 | 408.286 | 60.080 | 112.999 | 296.293 |
| | 2 | 406.270 | 60.080 | 112.999 | 294.278 |
| d17 | 0 | 424.313 | 60.080 | 112.999 | 312.324 |
| | 1 | 422.299 | 60.080 | 112.999 | 310.308 |
| | 2 | nd | nd | nd | Nd |
| d18 | 0 | 438.332 | 60.084 | 112.999 | 326.321 |
| | 1 | 436.316 | 60.084 | 112.999 | 324.307 |
| | $^{13}C_2D_2$ d18:1 | 440.334 | 60.080 | 112.999 | 328.325 |
| | 2 | 434.298 | 60.081 | 112.999 | 322.310 |
| t18 | 0 | 454.321 | 60.079 | 112.998 | 342.331 |
| d19 | 0 | 452.342 | 60.080 | 112.999 | 340.282 |
| | 1 | 450.324 | 60.086 | 112.999 | 338.340 |
| d20 | 0 | 466.362 | 60.079 | 112.999 | 354.368 |
| | 1 | 464.343 | 60.079 | 112.999 | 352.351 |
| t20 | 0 | 482.332 | 60.080 | 113.001 | 370.369 |
| | 1 | 480.336 | 60.079 | 112.999 | 368.348 |

TABLE 3b

| LCB-P | | m/z precursor | Product ions (m/z) | | |
|---|---|---|---|---|---|
| | | | A (neutral loss) | B | C** |
| d14 | 0 | 426.264 | 60.056 | 110.984 | 366.208 |
| | 1 | 424.249 | 60.056 | 110.984 | 364.193 |
| | 2 | 422.235 | 60.057 | 110.984 | 362.178 |
| d15 | 0 | 440.279 | 60.057 | 110.984 | 380.222 |
| | 1 | 438.263 | 60.058 | 110.984 | 38.205 |
| | 2 | Nd | nd | nd | Nd |
| d16 | 0 | 454.294 | 60.058 | 110.984 | 394.236 |
| | 1 | 452.278 | 60.058 | 110.984 | 392.220 |
| | 2 | 450.263 | 60.058 | 110.984 | 390.205 |
| d17 | 0 | 468.314 | 60.066 | 110.984 | 408.248 |
| | 1 | 466.297 | 60.059 | 110.984 | 406.238 |
| | 2 | 464.279 | 60.065 | 110.984 | 404.214 |
| d18 | 0 | 482.324 | 60.062 | 110.984 | 422.262 |
| | 1 | 480.309 | 60.062 | 110.984 | 420.247 |
| | $^{13}C_2D_2$ d18:1 | 484.330 | 60.020 | 110.984 | 424.310 |
| | 2 | 478.293 | 60.066 | 110.984 | 418.227 |
| t18 | 0 | 498.335 | 60.022 | 110.990 | 438.313 |
| d19 | 0 | 496.342 | 60.040 | 111.009 | 436.371 |
| | 1 | 494.325 | 60.041 | 111.009 | 434.284 |

TABLE 3b-continued

| LCB-P | | m/z precursor | Product ions (m/z) | | |
|---|---|---|---|---|---|
| | | | A (neutral loss) | B | C** |
| d20 | 0 | Nd | nd | nd | Nd |
| | 1 | 508.340 | 60.020 | 110.980 | 448.330 |
| t20 | 0 | 526.367 | 60.017 | 110.990 | 466.350 |
| | 1 | 524.3# | 60.0# | 110.9# | 464.0# |

This product ion information, collected using a high-resolution Time of flight mass spectrometer with high mass accuracy (<5 ppm), provides a firm basis for targeted approaches using tandem-MS. Scanning for neutral loss of m/z 60 (methylated amine group, fragment A) using a triple quadrupole mass spectrometer (with otherwise comparable analytical conditions) is a convenient mode to rapidly reveal LCB-Ps. Human plasma gave rise to strong signals of the d18 series (FIG. 2f), including the newly discovered 18:2 derivative (HCCO adduct at m/z 478.1, FIG. 2f) not known to have been described previously to our best knowledge.

We next extended our analysis to various biological species known to have different LCB (and thus possibly also LCB-P) inventories. Thus, the process was repeated using the samples extracted from human plasma, murine plasma and lymph, D. melanogaster and S. cerevisiae as described above.

S1P lyase is the key enzyme involved in the irreversible degradation of S1P; its impaired function in D. melanogaster (sply05091) leads to an accumulation of LCB-Ps 7. Here, with a starting sample of only five flies, we demonstrated a 200-fold accumulation in not only d14 and d16 (the major LCB-Ps in Drosophila), but also d15, d17, d18, d19 and d20 LCB-Ps in sply05091/sply05091 when compared with wild type (FIG. 2g, h). Genetic background effects were controlled for by also analyzing changes in heterozygous animals that resulted from a cross between sply05091 and a control strain, w1118 (wild type for sply). Heterozygous sply05091/+ showed much less extreme changes than sply/sply, suggesting that the differences in sply/sply were indeed due to the mutation rather than the genetic background. Finally, we established multiple reaction monitoring (MRM) conditions for quantification of LCB-P in extracts from different biological origins (FIG. 2i-m, Table 4) with a limit of detection of 0.3 fmol on the column at a signal-to-noise (S/N) ratio of 120 and 20 with and without IMP, respectively, in human plasma (FIG. 9). The overall levels measured for d18:1 S1P and 18:0 LCB-P in murine and human plasma corresponded well with published reports. Further, d18:2 LCB-P was present at levels comparable to SA1P (FIG. 2i). Lymph node (but not lymph fluid) is devoid of this form of LCB-P (FIG. 2j), which could be biologically relevant for the regulation of immune cell function in gradients of LCB-P 9. We show for the first time that baker's yeast (S. cerevisiae) contains LCB-P with double bonds (FIG. 2m) in addition to the reported fully saturated LCB-P.

Collectively, we have identified, characterized (co-elution with standard, exact mass, product ion analysis) and quantified ten LCB-P species not described previously and six LCB-P not known to be present in the tested biological samples, roughly doubling the number of known LCB-Ps (FIG. 2n, FIG. 12).

TABLE 4

LCB-P concentrations in different biological systems

| | H. sapiens plasma (μM) | M. musculus plasma (μM) | M. musculus Lymph (μM) | M. musculus lymph node (ng/LN) | M. musculus brain (pmol/mg) | D. melanogaster wt (pmol/mg) | S. cerevisiae (pmol/mg) |
|---|---|---|---|---|---|---|---|
| LCB-P d14:0 | | | | | | 0.436 ± 0.023 | |
| LCB-P d14:1 | | | | | | 0.796 ± 0.059 | |
| LCB-P d14:2 | | | | | | 0.223 ± 0.013 | |
| LCB-P d16:0 | | | | | | 0.248 ± 0.004 | 1.548 ± 0.151 |
| LCB-P d16:1 | 0.036 ± 0.003 | 0.029 ± 0.016 | | | | 0.068 ± 0.003 | |
| LCB-P d16:2 | | | | | | 0.043 ± 0.003 | |
| SA1P d18:0 | 0.136 ± 0.047 | 0.169 ± 0.051 | 0.035 ± 0.012 | 0.07 ± 0.004 | 0.904 ± 0.121 | 0.008 ± 0.001 | 0.439 ± 0.037 |
| S1P d18:1 | 0.728 ± 0.21 | 0.834 ± 0.232 | 0.228 ± 0.039 | 0.58 ± 0.14 | 4.554 ± 0.397 | | 1.488 ± 0.036 |
| LCB-P d18:2 | 0.125 ± 0.095 | 0.086 ± 0.029 | 0.027 ± 0.008 | | 0.196 ± 0.037 | | |
| LCB-P t18:0 | | | | | | | 3.196 ± 0.149 |
| LCB-P d20:0 | | | | | | | |
| LCB-P d20:1 | 0.002 ± 0.0002 | | | | 1.218 ± 0.422 | | 0.299 ± 0.011 |
| LCB-P t20:0 | | | | | | | 0.857 ± 0.063 |
| LCB-P t20:1 | | | | | | | 0.491 ± 0.015 |
| | n = 150 | n = 6 | n = 6 | n = 6 | n = 6 | n = 3 | n = 3 |

Example 15—Enrichment of Phosphate Diesters in a Mixture

The versatility of the polymer of the invention allows the isolation of different types of phospholipids. Thus, by changing the composition of the loading, washing and eluting solutions, different types of compounds (in addition to phosphate monoesters) can be separated or isolated.

In this example our data clearly show the possibility of separating different phosphate diesters containing lipids (like phosphatidylinositol, PI, and phosphatidylglycerol, DMPG) from phosphate monoesters (S1P), from other diesters (SM. DMPC, LPC) and non phosphorylated molecules (Cer, GluCer).

In this case the polymer is the polymer of Example 4a and the conditions used are:
Loading: isopropanol
Elution solvent 1: isopropanol/methanol
Elution solvent 2: Isopropanol/methanol/basic compound
Elution solvent 3: chloroform/methanol/acidic compound
By fine-tuning the composition of loading, washing and eluting solutions the specificity of the polymer can be changed accordingly so that not only phosphate monoester containing lipids but also other types of lipids can be enriched by the polymer material (see FIG. 11).

| Loading | Isopropanol 100% |
|---|---|
| Elution solvent 1 (washing) | Isopropanol:methanol |
| Elution solvent 2 (basic) | Isopropanol:methanol: triethylamine (49.5:49.5:1) |
| Elution solvent 2 (acidic) | Chloroform:methanol:1% trifluoroacetic acid (TFA) (49.5:49.5:1) |

The invention claimed is:

1. A polymer obtainable by radical co-polymerisation of a first monomer comprising a compound of general formula (I) or (II) or a mixture thereof:

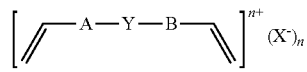
(I)

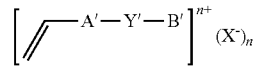
(II)

wherein each of A and A' is a 5- or 6-membered positively charged heteroaryl ring containing a quaternary nitrogen atom or when Y or Y' is —NR$^{20}$—(C=Z)—N—R$^{20}$—, A or A' is a 5- or 6-membered aryl or heteroaryl ring optionally substituted with halo, C$_{1-6}$ haloalkyl or nitro;

each of B and B' is a 5- or 6-membered positively charged heteroaryl ring containing a quaternary nitrogen atom; or a 5- or 6-membered aryl or heteroaryl ring optionally substituted with one or more substituents selected from halo, C$_{1-6}$ haloalkyl or nitro;

each of Y and Y' is a linking group comprising 1-6 —CH$_2$— units wherein a —CH$_2$— unit is optionally replaced by a C$_{5-14}$ aryl or heteroaryl group optionally substituted with one or more substituents selected from H, halogen, NH$_2$, C$_{1-4}$ alkyl, C$_{1-4}$ alkoxy, C$_{1-4}$ haloalkyl or C$_{1-4}$ haloalkoxy or when each of A or A' and B or B' is a 5- or 6-membered aryl or heteroaryl ring optionally substituted with one or more substituents selected halo, C$_{1-6}$ haloalkyl or nitro, each of Y and Y' may be —NR$^{20}$—(C=Z)—N—R$^{20}$—, wherein each R$^{20}$ is independently H, methyl or ethyl; and Z is O or S;

n is 1 or 2; or when Y and Y' is —NR$^{20}$—(C=Z)—N—R$^{20}$—, n is 0;

X$^-$ is a halide ion or a hydrophobic anion such as PF$_6^-$; with a second, cross-linking monomer and optionally with one or more further co-monomers;

wherein the molar ratio of the first monomer to the sum of the second monomer and the one or more further co-monomers (if present) is less than or equal to 1:5.

2. The polymer according to claim 1 wherein, in the monomer of general formulae (I) or (II), X$^-$ is a halide or a PF$_6^-$ ion.

3. The polymer according to claim 1 or claim 2 wherein, in the monomer of general formulae (I) or (II) the linking group Y is bonded to the quaternary nitrogen moiety of the group A or A'.

4. The polymer according to claim 1 wherein, in the monomer of general formula (I) or (II), the group A or A' is a pyridinium or imidazolium ion wherein:
   when A or A' is a pyridinium ion, the group —CH=CH$_2$ is connected at the pyridinium 4-position; and
   when A or A' is an imidazolium ion, the group —CH=CH$_2$ is linked to the non-quaternary ring nitrogen atom.

5. The polymer according to claim 1 wherein, in the monomer of general formula (I) or (ii), the group b or b' is a 5- or 6-membered positively charged heteroaryl ring containing a quaternary nitrogen atom wherein the linking group y is suitably bonded to the quaternary nitrogen moiety.

6. The polymer according to claim 5 wherein the group B or B' is a pyridinium or imidazolium ion.

7. The polymer according to claim 6 wherein B is a pyridinium ion and the group —CH=CH$_2$ is connected at the pyridinium 4-position; or
   B is an imidazolium ion and the group —CH=CH$_2$ is linked to the non-quaternary ring nitrogen atom.

8. The polymer according to claim 1, in the monomer of general formula (I), wherein A and B are the same and the monomer of general formula (I) is a compound of general formula (Ia) or (Ib):

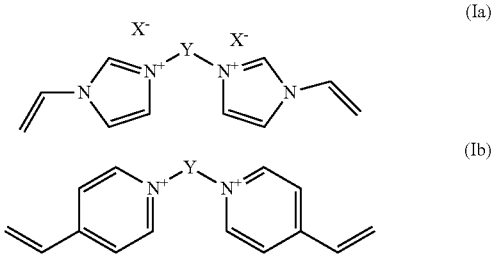

9. The polymer according to claim 8 wherein the monomer of general formula (I) is a monomer of formula (Ia).

10. The polymer according to claim 1 wherein, in the monomer of general formula (I) or (II), the group B or B' is a 5- or 6-membered aryl or heteroaryl ring.

11. The polymer according to claim 1 wherein, in the monomer of general formulae (I) or (II), Y is a linker group selected from:

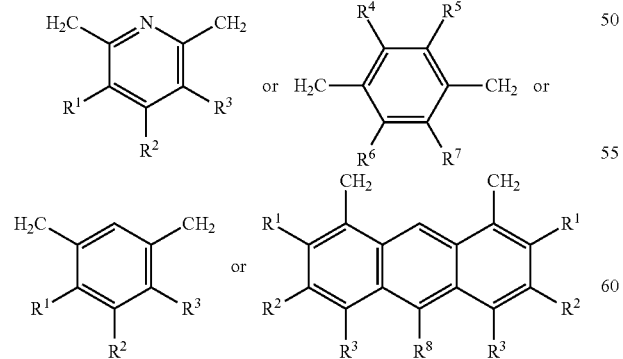

wherein
   each of R$^1$, R$^2$ and R$^3$ is independently selected from H, halogen, NH$_2$, C$_{1-4}$ alkyl, C$_{1-4}$ alkoxy, C$_{1-4}$ haloalkyl, C$_{1-4}$ haloalkoxy or R$^1$ and R$^2$ or R$^2$ and R$^3$ may together form a 5- or 6-membered carbocyclic, heterocyclic, aryl or heteroaryl ring;
   each of R$^4$, R$^5$, R$^6$ and R$^7$ is independently selected from H, halogen, NH$_2$, C$_{1-4}$ alkyl, C$_{1-4}$ alkoxy, C$_{1-4}$ haloalkyl, C$_{1-4}$ haloalkoxy or R$^4$ and R$^5$ or R$^6$ and R$^7$ may together form a 5- or 6-membered carbocyclic, heterocyclic, aryl or heteroaryl ring;
   R$^8$ is H, halogen, NH$_2$, C$_{1-4}$ alkyl, C$_{1-4}$ alkoxy, C$_{1-4}$ haloalkyl, C$_{1-4}$ haloalkoxy.

12. The polymer according to claim 11 wherein, in the monomer of general formula (I) or (II), Y is:

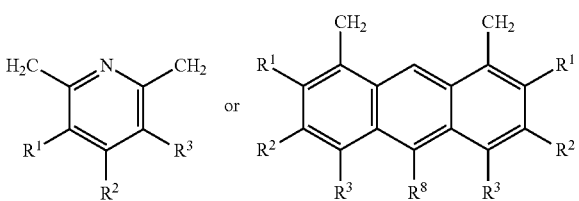

wherein each of R$^1$, R$^2$, R$^3$ and R$^8$.

13. The polymer according to claim 1 wherein the monomer of general formula (I) or formula (II) is Monomer 1, which has the structure:

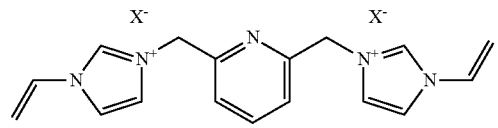

where X$^-$ is as defined in claim 1 but is most suitably Br$^-$; or

Monomer 2, which has the structure:

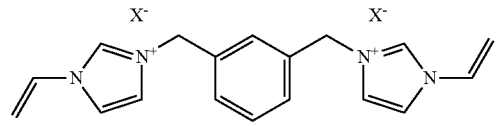

where X$^-$ is as defined in claim 1 but is most suitably Br$^-$; or

Monomer 3, which has the structure:

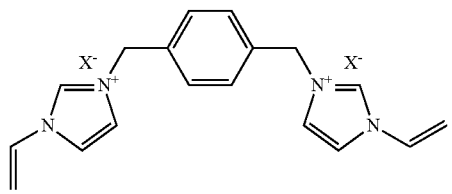

where X$^-$ is as defined above but is most suitably Br$^-$; or

Monomer 5, which has the structure:

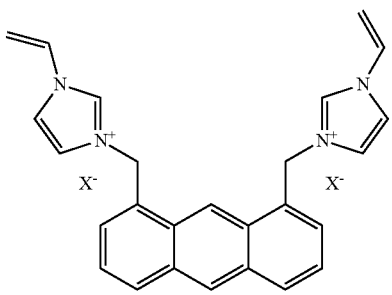

where X⁻ is as defined above but is most suitably Br⁻; or Monomer 4, which has the structure:

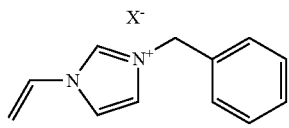

where X⁻ is as defined above but is most suitably Br⁻; or Monomer 6 which has the structure:

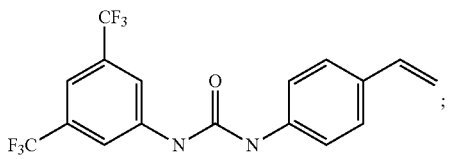 [SMILES: C=Cc1ccc(NC(=O)Nc2cc(C(F)(F)F)cc(C(F)(F)F)c2)cc1]

or a combination thereof.

14. The polymer according to claim 1 wherein the second cross linking monomer is selected from di- and tri-methacrylate monomers, dialkenyl benzene monomers and bis acrylamide monomers.

15. The polymer according to claim 14 wherein the second cross linking monomer is ethyleneglycol dimethacrylate (EGDMA), divinylbenzene (DVB), diisopropenylbenzene, (DIB), trimethylolpropanetrimethacrylate (TRIM), pentaerythritoltriacrylate (PETA), ethylenebisacrylamide (EBA), piperazinebisacrylamide (PBA), or methylenebisacrylamide (MBA).

16. The polymer according to claim 1 wherein the first monomer is Monomer 1 or a combination of Monomer 1 with one or more other monomers of general formula (I) or general formula (II); and the second monomer is EGDMA.

17. The process for the preparation of a polymer according to claim 1, the process comprising the radical co-polymerisation of a first monomer of general formula (I) or general formula (II) with a second, cross-linking monomer and optionally with one or more further co-monomers; characterised in that the molar ratio of the first monomer to the sum of the second monomer and the one or more further co-monomers (if present) is less than or equal to 1:5;

wherein the second, cross-linking monomer is ethyleneglycol dimethacrylate (EGDMA), divinylbenzene (DVB), diisopropenylbenzene, (DIB), trimethylolpropanetrimethacrylate (TRIM), pentaerythritoltriacrylate (PETA), ethylenebisacrylamide (EBA), piperazinebisacrylamide (PBA), or methylenebisacrylamide (MBA).

18. The process according to claim 17 wherein the molar ratio of the first monomer of general formula (I) or general formula (II) to the sum of the second monomer and the one or more further co-monomers (if present) is from 1:80 to 1:20.

19. A solid phase material comprising the polymer according to claim 1.

20. A separation device comprising the solid phase material according to claim 19.

21. The separation device according to claim 20 which comprises a chromatography column.

22. A kit for isolating phosphate ester compounds from a mixture comprising one or more such compounds, the kit comprising the solid phase material according to claim 19; instructions for the use of the material and optionally one or more standards.

* * * * *